United States Patent
Soetaert et al.

(10) Patent No.: US 9,650,658 B2
(45) Date of Patent: May 16, 2017

(54) METHODS TO PRODUCE BOLAAMPHIPHILIC GLYCOLIPIDS

(71) Applicant: Universiteit Gent, Ghent (BE)

(72) Inventors: Wim Soetaert, Lovendegem (BE); Inge Van Bogaert, Kalken (BE); Sophie Roelants, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/908,287

(22) PCT Filed: Aug. 7, 2014

(86) PCT No.: PCT/EP2014/067024
§ 371 (c)(1),
(2) Date: Jan. 28, 2016

(87) PCT Pub. No.: WO2015/028278
PCT Pub. Date: Mar. 5, 2015

(65) Prior Publication Data
US 2016/0168612 A1  Jun. 16, 2016

(30) Foreign Application Priority Data

Aug. 26, 2013 (EP) .................................. 13181722

(51) Int. Cl.
| | | |
|---|---|---|
| *C12N 15/80* | (2006.01) | |
| *C12P 19/44* | (2006.01) | |
| *C12P 19/12* | (2006.01) | |
| *C12P 7/64* | (2006.01) | |

(52) U.S. Cl.
CPC .............. *C12P 19/44* (2013.01); *C12N 15/80* (2013.01); *C12P 7/64* (2013.01); *C12P 19/12* (2013.01)

(58) Field of Classification Search
None
See application file for complete search history.

(56) References Cited

U.S. PATENT DOCUMENTS

2013/0035403 A1  2/2013  Schaffer et al.
2013/0089892 A1  4/2013  Soetaert et al.

FOREIGN PATENT DOCUMENTS

| WO | 2011061032 A1 | 5/2011 |
|---|---|---|
| WO | 2011154523 A1 | 12/2011 |
| WO | 2012080116 A1 | 6/2012 |
| WO | 2013092421 A1 | 6/2013 |
| WO | 2015028278 A1 | 3/2015 |

OTHER PUBLICATIONS

Saerens et al. (I), Biotechnology and Bioengineering, vol. 108, No. 12, Dec. 2011, pp. 2923-2931.*
Brakemeier et al., Novel Sophorose Lipids From Microbial Conversion of 2-Alkanols, Biotechnology Letters, Jan. 1, 1995, pp. 1183-88, vol. 17, No. 11.
Saerens et al., Cloning and functional characterization of the UDP-glucosyltransferase UgtB1 involved in sophorolipid production by Candida bombicola and creation of a glucolipid-producing yeast strain, Yeast, Apr. 1, 2011, pp. 279-292, vol. 28, No. 4.
Price et al., Structural characterization of novel sophorolipid biosurfactants from a newly identified species of Candida yeast, Carbohydrate Research, Feb. 1, 2012, pp. 33-41, vol. 348.
Van Bogaert et al., The biosynthetic gene cluster for sophorolipids: a biotechnological interesting biosurfactant produced by Starmerella bombicola, Molecular Microbiology, Mar. 21, 2013, pp. 501-509, vol. 88, No. 3.
PCT International Search Report, PCT/EP2014/067024, dated Jul. 11, 2014.
PCT International Written Opinion, PCT/EP2014/067024, dated Jul. 11, 2014.

* cited by examiner

*Primary Examiner* — Irene Marx
(74) *Attorney, Agent, or Firm* — TraskBritt P.C.

(57) ABSTRACT

This disclosure relates to the field of the microbial production of specific types of glycolipids that are potentially useful as replacements for petroleum-based detergents and emulsifiers. This disclosure, more specifically, discloses the usage of yeasts having a dysfunctional acetyltransferase for producing high amounts of bolaamphiphilic glycolipids when using conventional and cheap substrates. Furthermore, the disclosure relates to yeasts having a dysfunctional acetyltransferase optionally combined with a dysfunctional lactonase and/or second glucosyltransferase. The latter microorganisms are capable of producing high amounts of bolaamphiphilic sophorolipids.

14 Claims, 12 Drawing Sheets

METHODS TO PRODUCE BOLAAMPHIPHILIC GLYCOLIPIDS

CROSS-REFERENCE TO RELATED APPLICATIONS

This application is a national phase entry under 35 U.S.C. §371 of International Patent Application PCT/EP2014/067024, filed Aug. 7, 2014, designating the United States of America and published in English as International Patent Publication WO 2015/028278 A1 on Mar. 5, 2015, which claims the benefit under Article 8 of the Patent Cooperation Treaty to European Patent Application Serial No. 13181722.3, filed Aug. 26, 2013.

TECHNICAL FIELD

The application relates to the field of the microbial production of specific types of glycolipids that are potentially useful as replacements for petroleum-based detergents and emulsifiers. This disclosure more specifically discloses the usage of yeasts having a dysfunctional acetyltransferase for producing high amounts of bolaamphiphilic glycolipids when using conventional and cheap substrates. Furthermore, the application relates to yeasts having a dysfunctional acetyltransferase optionally combined with a dysfunctional lactonase and/or second glucosyltransferase. The latter microorganisms are capable of producing high amounts of bolaamphiphilic sophorolipids.

BACKGROUND

The non-pathogenic yeast *Starmerella bombicola* (formerly known as *Candida bombicola*), ATCC 22214 (CBS 6009), is commercially applied for the production of sophorolipids (FIG. 1). Ideally, production of sophorolipids involves the presence of an easily metabolized carbohydrate such as glucose and an oil or fatty acid (e.g., vegetable oil) as, respectively, the hydrophilic and hydrophobic carbon source. These can be considered as the conventional carbon sources applied in sophorolipid production.

Common sophorolipids are comprised of a sophorose head group (2-O-β-D-glucopyranosyl-D-glucopyranose) attached to a (sub)terminal hydroxylated $C_{18}$ or $C_{16}$ fatty acid by a glycosidic linkage between the anomeric C-atom of the sugar and the hydroxyl group of the fatty acid. Sophorolipids are always comprised of a mixture of structurally related molecules with variation in: 1) degree of fatty acid saturation (saturated, mono-unsaturated or di-unsaturated), 2) presence or absence of acetyl groups at C6' and/or C6" atoms, 3) lactonization between the carboxyl end of the fatty acid and either the C4", C6' or C6" atom of the sophorose group resulting in a lactonic sophorolipid or absence of this lactonization resulting in an open or acidic sophorolipid, 4) fatty acid chain length, and 5) (ω) or (ω-1) hydroxylation of the fatty acid (Asmer et al., 1988). Due to this structural variation, sophorolipids show many interesting applications in a wide range of industrial fields (Banat et al., 2010; Franzetti et al., 2010; Kralova and Sjoblom, 2009; and Mulligan, 2009). Since the structural composition of sophorolipids is reflected in the physico-chemical properties, several industries are particularly interested in specific structural variants.

WO 2012/080116 and Saerens et al. (2011b) disclose that yeast strains that are mutated in a gene encoding for an acetyltransferase (at; GenBank accession number HQ670751) are capable of producing a mixture of entirely unacetylated sophorolipids. This acetyltransferase is solely responsible for the acetylation of the sophorolipid molecules at the C6' and/or C6" atoms. The unacetylated molecules produced by the knock-out strain display better water solubility and foam-forming capacities.

As explained above, common sophorolipids consist of two glucose molecules forming sophorose with a hydrophobic fatty acid chain attached to it. However, in some exceptional conditions, minor amounts of glycolipids with additional glucose molecules can be detected. The supplementary glucose molecule(s) are found at the other end of the alkyl chain, in this way creating bolaamphiphilic or bolaform molecules, molecules with two hydrophilic parts connected by a hydrophobic spacer. Bolaform surfactants recently attracted a lot of attention due to their unique configuration: a long hydrophobic spacer with hydrophilic groups at both ends. This makes the molecule more water soluble, but still allows formation of micelles, vesicles and other laminar structures. The best known examples of a natural bolaform are the tetraether lipids present in membranes of archaea able to grow under extreme temperatures and salt concentrations. These bolaforms strongly stabilize the membranes under extreme conditions.

The production of bolaform glycolipids appears insufficient and/or expensive. Brakemeier et al. (1995 and 1998) were the first to report on the presence of bolaform sophorolipids when 2-alkanols, such as 2-tetradecanol and 2-dodecanol, were used as rather unconventional hydrophobic carbon sources. Based on the composition of the sophorolipids, Brakemeier obtained a relative amount of these molecules in the total mixture lower than 7.4% when produced from 2-tetradecanol and lower than 0.5% when produced from 2-dodecanol. In other words, despite the use of non-conventional and expensive substrates, the overall obtained amount of these bolaform molecules was still very low.

Recently, Price et al. (2012) described the production of novel sophorolipids by the species *Candida* sp. NRRL Y-27208 when grown on a normal production medium (fatty acids as the hydrophobic carbon source). Among the novel sophorolipids, 17 dimeric (=comprising 4 glucose molecules) and trimeric (=comprising 6 glucose molecules) sophoroses were identified. Dimeric molecules were also reported for *Starmerella* (*Candida*) *bombicola*. The authors state that these compounds were produced only in minor amounts, close to the detection limit. The majority of the sophorolipids were the conventional ones as shown in FIG. 1.

Taken together, to date, bolaform glycolipids can only be obtained in minor amounts when using conventional hydrophobic carbon sources. The use of unconventional substrates can only lead to a slight increase of the bolaform moiety. Moreover, the latter process is uneconomical due to the use of the very expensive special substrates. Hence, there is a need to efficiently produce bolaamphiphilic sophorolipids in significant amounts starting from cheap conventional carbon sources.

BRIEF SUMMARY

Disclosed is that acetyltransferase negative-yeast strains are surprisingly able to produce significant amounts of bolaamphiphilic glycolipids.

This disclosure relates in the first instance to the usage of a fungal strain to produce bolaamphiphilic glycolipids wherein the fungal strain comprises a dysfunctional acetyltransferase.

The disclosure further relates to the latter usage wherein the fungal strain further comprises a dysfunctional lactonase or wherein the microbial strain further comprises a dysfunctional second glucosyltransferase or wherein the fungal strain further comprises both a dysfunctional lactonase and a dysfunctional second glucosyltransferase.

This disclosure specifically relates to the latter usages wherein the fungal strain is a fungal strain capable of producing glycolipids. More specifically, the disclosure relates to the latter usages wherein the fungal strain capable of producing glycolipids is a yeast selected from the group consisting of *Starmerella* (*Candida*) *bombicola*, *Candida apicola*, *Candida batistae*, *Candida floricola*, *Candida riodocensis*, *Candida stellate*, *Candida kuoi*, *Candida* sp. NRRL Y-27208, *Rhodotorula bogoriensis* sp., *Wickerhamiella domericqiae* and a sophorolipid-producing strain of the *Starmerella* clade. Even more specifically, this disclosure concerns the latter usages wherein the *Starmerella bombicola* is the strain *Starmerella bombicola* ATCC 22214 or strains derived therefrom.

In another aspect, this disclosure relates to a method of producing bolaamphiphilic glycolipids comprising:
- providing a fungal strain comprising a dysfunctional acetyltransferase,
- culturing the fungal strain in order to obtain a fermentation broth comprising a mixture of several types of glycolipids, and
- recovering the bolaamphiphilic glycolipids from the fermentation broth.

The disclosure also relates to a method as indicated above wherein the fungal strain further comprises a dysfunctional lactonase, a dysfunctional second glucosyltransferase, or both a dysfunctional lactonase and a dysfunctional second glucosyltransferase.

Furthermore, this disclosure relates to methods as indicated above wherein (cheap) conventional substrates are used during culturing of a fungal strain in order to obtain a fermentation broth.

The disclosure further relates to methods as described above wherein the bolaamphiphilic glycolipids are recovered from the fermentation broth with an organic solvent. More specifically, this disclosure relates to methods as described above wherein the organic solvent comprises methanol and/or ethanol. In addition, the disclosure relates to methods as indicated above wherein the bolaamphiphilic glycolipids are recovered from the fermentation broth using membrane filtration techniques such as ultrafiltration or diafiltration.

This disclosure further relates to methods as described above wherein the dysfunctional acetyltransferase, lactonase and/or second glucosyltransferase is obtainable by: 1) mutating the gene encoding for the acetyltransferase, lactonase and/or glucosyltransferase, or 2) silencing transcription or translation of the gene encoding for the acetyltransferase, lactonase and/or glucosyltransferase, or 3) disrupting the function of the acetyltransferase, lactonase and/or glucosyltransferase.

The disclosure more specifically relates to methods as described above wherein the fungal strain has: i) a dysfunctional acetyltransferase or a dysfunctional acetyltransferase and a dysfunctional lactonase, and wherein the bolaamphiphilic glycolipids are non-acetylated bolaamphiphilic sophorolipids consisting of four glucose molecules, or has ii) a dysfunctional acetyltransferase and a dysfunctional second glucosyltransferase or a dysfunctional acetyltransferase, a dysfunctional second glucosyltransferase and a dysfunctional lactonase, and wherein the bolaamphiphilic glycolipids are non-acetylated bolaamphiphilic glycolipids consisting of two glucose molecules.

More specifically, this disclosure also relates to methods as described above wherein the total amount of the bolaamphiphilic sophorolipids is at least 10% of the total amount of the mixture of several types of glycolipids.

The disclosure further relates to a method of producing sophorose and acidic sophorolipids comprising performing an alkaline hydrolysis of the bolaamphiphilic glycolipids obtainable by a method as described above.

This disclosure also relates to a method of producing symmetric bolaamphiphilic glycolipids comprising:
- providing a fungal strain comprising a dysfunctional acetyltransferase, or comprising a dysfunctional acetyltransferase and a dysfunctional lactonase, or comprising a dysfunctional acetyltransferase and a dysfunctional cytochrome P450 monooxygenase, or comprising a dysfunctional acetyltransferase, a dysfunctional lactonase and a dysfunctional cytochrome P450 monooxygenase,
- culturing the fungal strain using fatty alcohols and/or diols as a substrate in order to obtain a fermentation broth comprising a mixture of several types of glycolipids, and
- recovering the symmetric bolaamphiphilic glycolipids from the fermentation broth, wherein the symmetric bolaamphiphilic glycolipids are molecules having a hydrophobic spacer with hydrophilic glucose molecules at both ends of the spacer, wherein the hydrophilic glucose molecules are linked to both sides of the spacer by a glycosidic bond, and wherein the fungal strain is a yeast selected from the group consisting of *Starmerella* (*Candida*) *bombicola*, *Candida apicola*, *Candida batistae*, *Candida floricola*, *Candida riodocensis*, *Candida stellate*, *Candida kuoi*, *Candida* sp. NRRL Y-27208, *Rhodotorula bogoriensis* sp., *Wickerhamiella domericqiae* and a sophorolipid-producing strain of the *Starmerella* clade.

DETAILED DESCRIPTION

Figure 1:
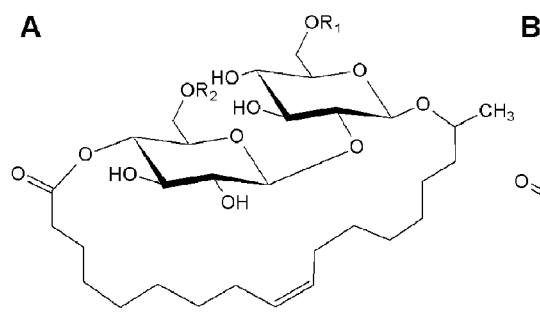
FIG. 1: Standard sophorolipid molecules found as major compounds in the natural mixture produced by the wild-type yeast. (Panel A) Lactonic form; (Panel B) acidic form. $R_1$=H or $COCH_3$, $R_2$=H or $COCH_3$.
Figure 1:
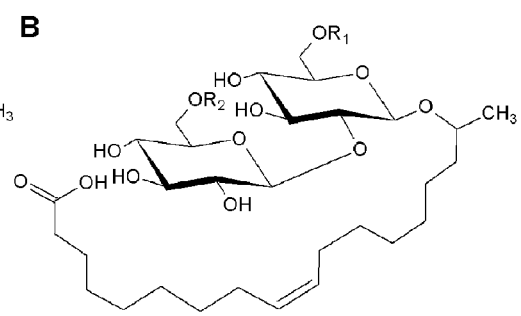

Microbial produced bolaamphiphilic glycolipids are rare and are produced in very low amounts when using conventional substrates such as glucose and/or vegetable oil (see Price et al. 2012). Alternatively, one can produce similar, but structurally different bolaform sophorolipids by using unconventional and expensive carbon sources such as secondary alcohols. However, also in this later case, these molecules make up only a marginal fraction of the total glycolipids mixture (see Brakemeier et al., 1995 and 1998)

This disclosure describes a new manner of producing these bolaform molecules in high concentrations starting from conventional and cheap hydrophobic carbon sources such as vegetable oils.

WO2012/080116 and Saerens et al. (2011b) disclosed that yeast strains that are mutated in a gene encoding for an acetyltransferase (at; GenBank accession number HQ670751) produce non-acetylated sophorolipids.

The disclosure surprisingly discloses that when producing sophorolipids with this previously described strain (i.e., knocked-out in the sophorolipid acetyltransferase (=Δat)) and when specifically analyzing the full fermentation broth, that glycolipids with hydrophilic moieties at both sites of a fatty acid chain (=so-called bolaform glycolipids or bolaamphiphilic glycolipids or molecules having a hydrophobic spacer with hydrophilic glucose molecules at both ends of the spacer) can also be obtained. Moreover, and unexpectedly, these molecules were not present as marginal compounds as described previously, but represent more than 10% or higher (i.e., 20%, 30%, . . . , 80%, 90%) of the total glycolipid mixture present in the fermentation broth. These bolaform molecules are more hydrophilic and, consequently, more water soluble compared to the conventional sophorolipids and have the tendency to increase viscosity. This latter feature is, among others, useful for the creation of water-containing creams used in cosmetics, pharmaceuticals and personal care products. Furthermore, this property is desired in certain food applications. These types of molecules also have potential in the induction of commercial cellulase production by fungal species.

The structure of these molecules can be confirmed by, for example, NMR to be bolaamphiphilic.

More surprisingly, this disclosure further demonstrates that the total production of glycolipids and the relative amount of the bolaform sophorolipids can be even further increased by using a yeast strain (such as a *Starmerella bombicola* strain) that is not solely knocked-out in the acetyltransferase gene as described above, but is also knocked-out in the lactonase gene. This double knock-out strain (i.e., ΔatΔlac) is surprisingly performing better than the single acetyltransferase knock-out strain (Δat). In sharp contrast, a strain with a single knock out of this lactonase (Δlac) is not producing these types of molecules (see Table 1). The lactonase gene is described in detail in WO 2013/092421 and the nucleotide and amino acid sequence can be consulted under GenBank accession number KC 121031.

TABLE 1

Overview of certain *S. bombicola* strains and their ability to produce bolaform glycolipids

| Strain | bolaform glycolipids detectable (Y/N) | Quantities |
| --- | --- | --- |
| wild type | N | / |
| Δat | Y | low |
| ΔatΔlac | Y | high |
| Δlac | N | / |
| Δugtb 1 Δat | Y | low |

Figure 2:
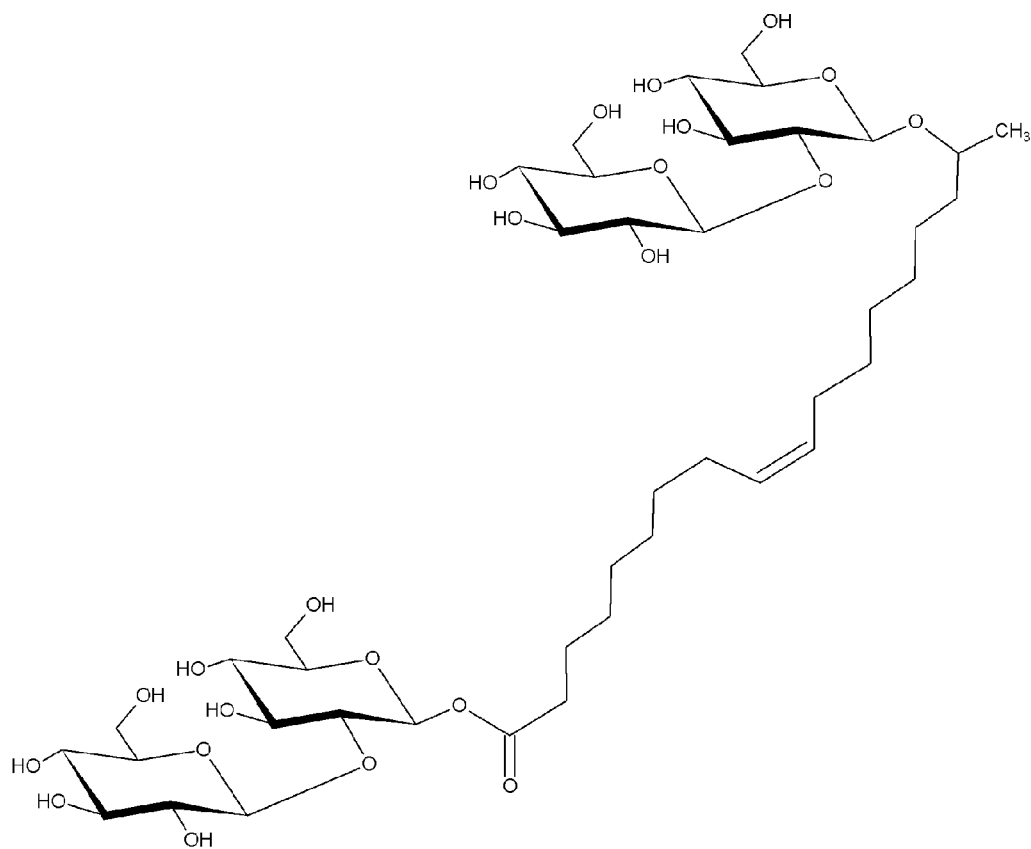
FIG. 2: Bolaform sophorolipid molecule comprising four glucose molecules.

The disclosure thus relates to the production of glycolipids having a bolaamphiphilic character, meaning that two hydrophilic moieties such as glucose are present. More specifically, this means that the known sophorolipid backbone is a non-acetylated 2-O-β-D-glucopyranosyl-D-glucopyranose unit (sophorose) attached β-glycosidically to a terminal or subterminal hydroxylated fatty acid. To this molecule, two additional glucose molecules forming the disaccharide sophorose are attached, more, in particular, by an ester bound to the carboxyl function of the fatty acid (see FIG. 2). The fatty acid chain length, in general, varies between 16 and 18 carbon atoms having one, two, or no unsaturations, but is not limited to this profile.

Figure 7:
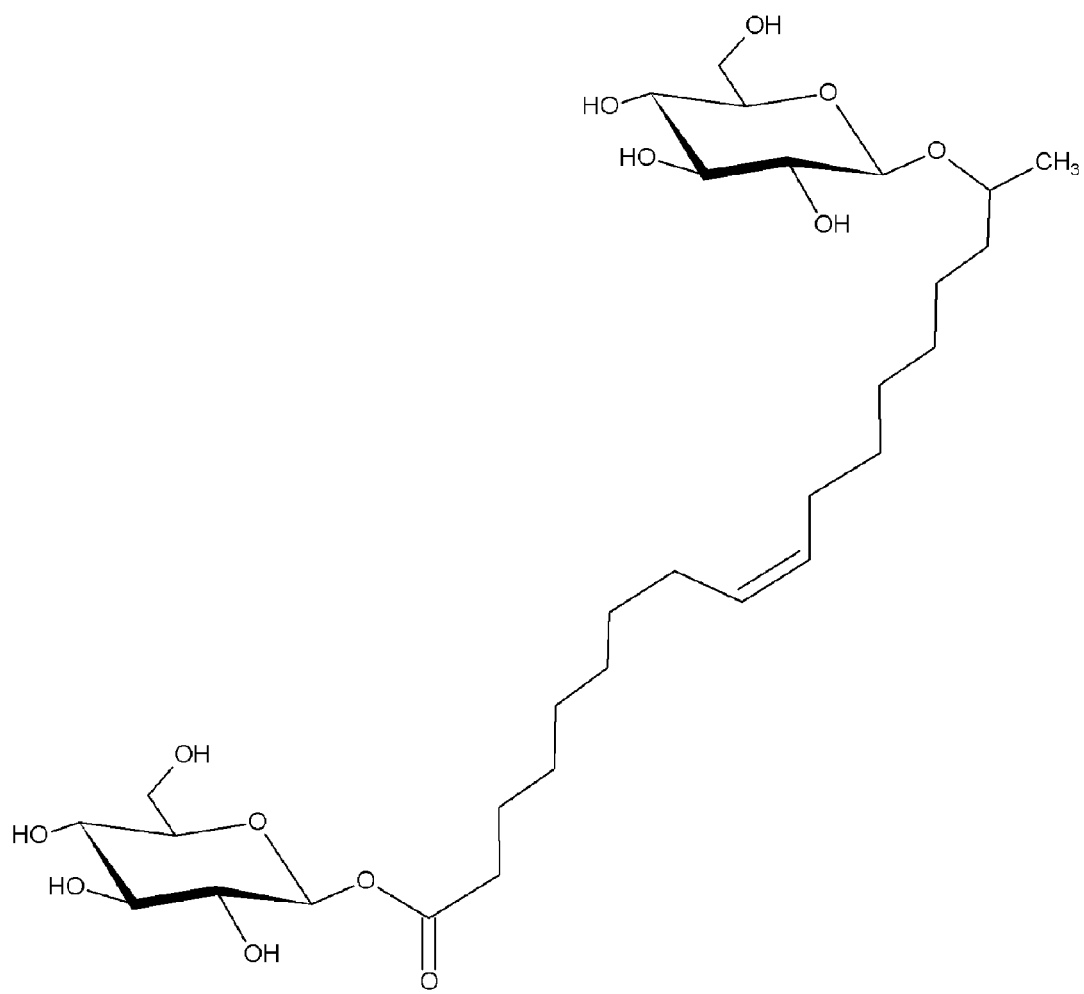
FIG. 7: Bolaform glycolipid molecule comprising two glucose molecules produced by a ΔugtB1 Δat strain.

Furthermore, this disclosure further relates to the production of bolaform glycolipids with one glucose molecule at each site of the hydrophobic spacer (see FIG. 7 and Table 1). Such molecules can be obtained by using a Δugtb1 Δat strain: an acetyltransferase negative strain with, in addition, a dysfunctional second glucosyltransferase (=ugtb1). This later gene is described in detail in WO 2011/154523A1 and the GenBank accession number is HM440974.

Hence, the disclosure relates in the first instance to the usage of a fungal strain to produce bolaamphiphilic glycolipids wherein the fungal strain comprises a dysfunctional acetyltransferase.

This disclosure further relates to the latter usage wherein the fungal strain further comprises a dysfunctional lactonase or wherein the fungal strain further comprises a dysfunctional second glucosyltransferase or wherein the fungal strain further comprises both a dysfunctional lactonase and a dysfunctional second glucosyltransferase.

The term "fungal strain" refers to any genetic variant or sub-type of a particular fungus, such as a yeast strain, that is capable of producing sophorolipids. In other words, the disclosure relates to a usage as described above wherein the fungal strain is a fungal strain capable of producing sophorolipids endogenously or after genetic modification. More specifically, this fungal strain is a fungal species comprising, but not limited to: *Candida apicola* (Gorin et al., 1961), which was initially identified as *C. magnolia*, *C. bombicola* (Spencer et al., 1970), *Wickerhamiella domericqiae* (Chen et al., 2006), *Rhodotorula bogoriensis* (Tulloch et al., 1968), *Candida batistae* (Konishi et al., 2008), *Candida floricola* (Imura et al., 2010), *Candida riodocensis*, *Candida stellate* and *Candida* sp. NRRL Y-27208 (Kurzman et al., 2010), *Candida kuoi* (Kurtzman, 2012) and any other strain of the *Starmerella* clade. This disclosure more specifically relates to a usage as described above wherein the *Starmerella* (*Candida*) *bombicola* is the strain *Starmerella* (*Candida*) *bombicola* ATCC 22214 (CBS 6009) or strains derived therefrom.

A "genetically modified fungal strain" producing sophorolipids refers to any fungal strain that is genetically engineered so that the strain produces sophorolipids or sophorolipid-like molecules.

The term "sophorolipid-like molecules" refers to a glycolipid consisting of one or more sophorose moieties linked to one or more (hydroxylated) fatty acids. Furthermore, this term also relates to glycolipids without a clear sophorose unit, but with a backbone based on the native sophorolipids: a glucopyranose unit attached β-glycosidically to a terminal or subterminal hydroxylated fatty acid.

The disclosure further relates to a dysfunctional acetyltransferase (at) and, optionally, also to a dysfunctional lactonase (lac), dysfunctional second glucosyltransferase (ugtb1) and/or dysfunctional cytochrome P450 monooxygenase (cyp52m1). The term "dysfunctional" means, in general, a gene or protein that is not performing "normally," and/or has an absent or impaired function. The term thus refers to a gene or protein that is: a) not functional because it is not present, b) still present but is rendered non-functional or c) that is present but has a weakened or reduced function. The term "dysfunctional" specifically refers to a gene having lost its capability to encode for a fully functional acetyltransferase, lactonase, cytochrome P450 monooxygenase and/or second glucosyltransferase, or a polypeptide/protein having lost its acetyltransferase, lactonase, cytochrome P450 monooxygenase and/or second glucosyltransferase activity, either completely or partially. "Partially" means that the activity of the latter enzymes, measured by any method known in the art, is significantly lower (p<0.05) when compared to the activity of the wild-type counterparts of the enzymes.

A "dysfunctional" nucleic acid molecule as defined above can be obtained by mutation or by any known means to silence the transcription or translation of the nucleic acid. The latter means comprises the insertion of a nucleic acid fragment, a marker gene or any other molecule in the functional coding or non-coding part of the target gene, a mutation or removal of the functional coding or non-coding part of the target gene, the usage of specific siRNAs, miRNAs, or combinations thereof, or any other means known to a skilled person.

The term "mutation" refers to a spontaneous mutation and/or to an induced mutation in the genome of the fungal strain. The mutation can be a point mutation, deletion, insertion or any other type of mutation.

Similarly, a "dysfunctional" polypeptide as defined above can be obtained by any (small) compound or other means to weaken or disrupt the function of the target genes of this disclosure. Means to silence the transcription or translation or means to disrupt the function of the target genes of the disclosure or means to disrupt the function of a necessary regulator/activator protein of the target genes comprise the usage of any molecule such as, but not limited to, an antibody, an amino acid, a peptide, a small molecule, an aptamer, a ribozyme, an oligoribonucleotide sequence such as a dsRNA used to initiate RNA interference (RNAi) or an anti-sense nucleic acid. Such a molecule is thus capable to bind on a target protein or an activator/regulator protein thereof or is capable of interfering with the cellular synthesis of the target enzyme or of an activator/regulator thereof by, for example, binding and degrading mRNAs encoding for a target protein or an activator/regulator thereof.

A "dysfunctional" acetyltransferase, lactonase, second glucosyltransferase and/or cytochrome P450 monooxygenase thus also refers to an enzyme with reduced activity, obtained by any method known by the person skilled in the art. Non-limiting examples of the methods are the introduction of point mutations, the usage of truncated or mutated enzymes, the usage of inhibitors or antibodies, and any of the methods described above.

The term "dysfunctional" thus also refers to the absence of the specific genes mentioned above (acetyltransferase, lactonase, second glucosyltransferase or cytochrome P450 monooxygenase gene) in the genome of the applied fungal strain. This is of particular interest in the case of heterologous sophorolipid production by hosts naturally lacking some or all of the sophorolipid genes.

This disclosure thus relates to a dysfunctional acetyltransferase, lactonase, second glucosyltransferase and/or cytochrome P450 monooxygenase that are obtainable by: 1) mutating the gene encoding for acetyltransferase, lactonase, second glucosyltransferase and/or cytochrome P450 monooxygenase, or 2) silencing transcription or translation of the gene encoding for acetyltransferase, lactonase, second glucosyltransferase and/or cytochrome P450 monooxygenase, or 3) disrupting the function of acetyltransferase, lactonase, second glucosyltransferase and/or cytochrome P450 monooxygenase.

In another aspect, the disclosure relates to a method of producing bolaamphiphilic glycolipids comprising:
providing a microbial strain comprising a dysfunctional acetyltransferase,
culturing the microbial strain in order to obtain a fermentation broth comprising a mixture of several types of glycolipids, and
recovering the bolaamphiphilic glycolipids from the fermentation broth.

The disclosure also relates to a method as indicated above wherein the microbial strain further comprises a dysfunctional lactonase, a dysfunctional second glucosyltransferase, or both a dysfunctional lactonase and a dysfunctional second glucosyltransferase.

Furthermore, this disclosure relates to methods as indicated above wherein (cheap) conventional substrates are used during culturing of a fungal strain in order to obtain a fermentation broth.

This disclosure further relates to methods as described above wherein the bolaamphiphilic glycolipids are recovered from the fermentation broth with an organic solvent. More specifically, the disclosure relates to methods as described above wherein the organic solvent comprises methanol and/or ethanol, such as, but not limited to, an organic solvent comprising water and ethanol.

In addition, this disclosure relates to methods as indicated above wherein the bolaamphiphilic glycolipids are recovered from the fermentation broth using membrane filtration techniques such as ultrafiltration or diafiltration. Preferably, sequential ultrafiltration procedures are used (as are, for example, described further in Example 7).

The terms "culturing the fungal strain" refers to growing the strain under conditions and in medium known by the person skilled in the art that will result in the production of glycolipids in sufficient yields. Sophorolipid production is optimal when both a hydrophilic and a hydrophobic carbon source are applied. More in particular, the production of sophorolipids involves the presence of an easily metabolized carbohydrate such as glucose and an oil or fatty acid (e.g., vegetable oil such as rapeseed oil) as, respectively, the hydrophilic and hydrophobic carbon source.

"Conventional substrates" refer to cheap carbon sources such as carbohydrates (such as glucose), fatty acids and vegetable oils (such as rapeseed oil) that are, respectively, used as the hydrophilic and hydrophobic carbon source. This is in contrast to more expensive secondary alcohols or ketons that are, in some cases, applied as the hydrophobic carbon source.

The bolaform glycolipid molecules described in the disclosure cannot be extracted from the culture or fermentation broth with the established ethyl acetate extraction method. Hence, the terms "recovering bolaamphiphilic glycolipids from the fermentation broth" refers to any method resulting in the recovery of molecules with a more hydrophilic nature compared to the conventional sophorolipids, such as bolaamphiphilic glycolipids. For example, but not limited to, "recovery of the bolaform sophorolipids" can be achieved by using ethanol, methanol, water and/or mixtures thereof. Alternatively, bolaamphiphilic glycolipids can also be recovered from the fermentation broth using membrane filtration techniques such as ultrafiltration or diafiltration. These techniques allow retention of molecules with a certain molecular weight (e.g., the bolaform sophorolipids), while the smaller ones such as salts, sugars, small proteins, etc., pass the membrane. Combined filtration steps with membranes with different pore size can allow for the selection of molecules with the targeted molecular weight. For instance, in one step, the bolaform glycolipids will be retained in order to separate them from the smaller molecular weight molecules, while in the other step (before or after), the bolaform glycolipids are allowed to pass while the bigger molecules (e.g., large proteins and polysaccharides) are retained.

This disclosure more specifically relates to methods as described above wherein the fungal strain has: i) a dysfunctional acetyltransferase or a dysfunctional acetyltransferase and a dysfunctional lactonase, and wherein the bolaamphiphilic glycolipids are non-acetylated bolaamphiphilic sophorolipids consisting of four glucose molecules, or has ii) a dysfunctional acetyltransferase and a dysfunctional second glucosyltransferase, or a dysfunctional acetyltransferase, a dysfunctional second glucosyltransferase and a dysfunctional lactonase, and wherein the bolaamphiphilic glycolipids are non-acetylated bolaamphiphilic glycolipids consisting of two glucose molecules. Specific examples of the latter methods are described further in the Examples section.

The disclosure also relates to methods as described above wherein the total amount of the bolaamphiphilic sophorolipids is at least 10% of the total amount of the mixture of several types of glycolipids. The terms "at least 10%" refer to 10%, 20%, 30%, 40%, 50%, 60%, 70%, 80%, 90%, 95% or 99% of the total amount of the mixture of several types of glycolipids. More specifically, the latter terms refer to "10%" when a $\Delta$ugtb1 $\Delta$at strain is used to produce bolaform sophorolipids with one glucose at each site, or, refer to "40%" when a $\Delta$at strain is used to produce bolaform sophorolipids comprising four glucose molecules (i.e., two glucoses at each site), or refer to "85%" when a $\Delta$at$\Delta$lac strain is used to produce bolaform sophorolipids comprising four glucose molecules (i.e., two glucoses at each site).

Because the described bolaform sophorolipids or bolaamphiphilic glycolipids consist of acidic sophorolipids coupled to a second sophorose molecule by an ester bond, an "asymmetric" molecule is created. In other words, the chemical bound that connects the two sophorose molecules to the fatty acid spacer is different, i.e., a glycosidic versus an ester bound. Moreover, sophorose is a disaccharide that cannot be produced in a cheap way. Also, the production of acidic sophorolipids, as described, via using a knock-out strain of the lactonesterase (WO 2013/092421), might not be straightforward. The thus rather "asymmetric" bolaform sophorolipids of this disclosure offers an alternative way of obtaining acidic sophorolipids, while at the same time, releasing the rare disaccharide sophorose. This process thus represents an alternative and cheaper way of producing sophorose. Because sophorose is smaller (342 Dalton), as compared to acidic sophorolipids (622 Dalton), and with the extra fact that sophorolipids will form macromolecular aggregates, these two molecules might be separated by using ultrafiltration or, alternatively, ion exchange and/or extraction methods could be applied.

This disclosure thus further relates to a method of producing sophorose and acidic sophorolipids comprising performing an alkaline hydrolysis of the bolaamphiphilic glycolipids obtainable by a method as described above. With the term "alkaline hydrolysis" is meant the cleavage of the above-indicated ester bond by applying a pH greater than 7 (=for example, pH 8, 9 or 10 . . . ), resulting in a detached sophorose and an acidic sophorolipid.

Figure 15:
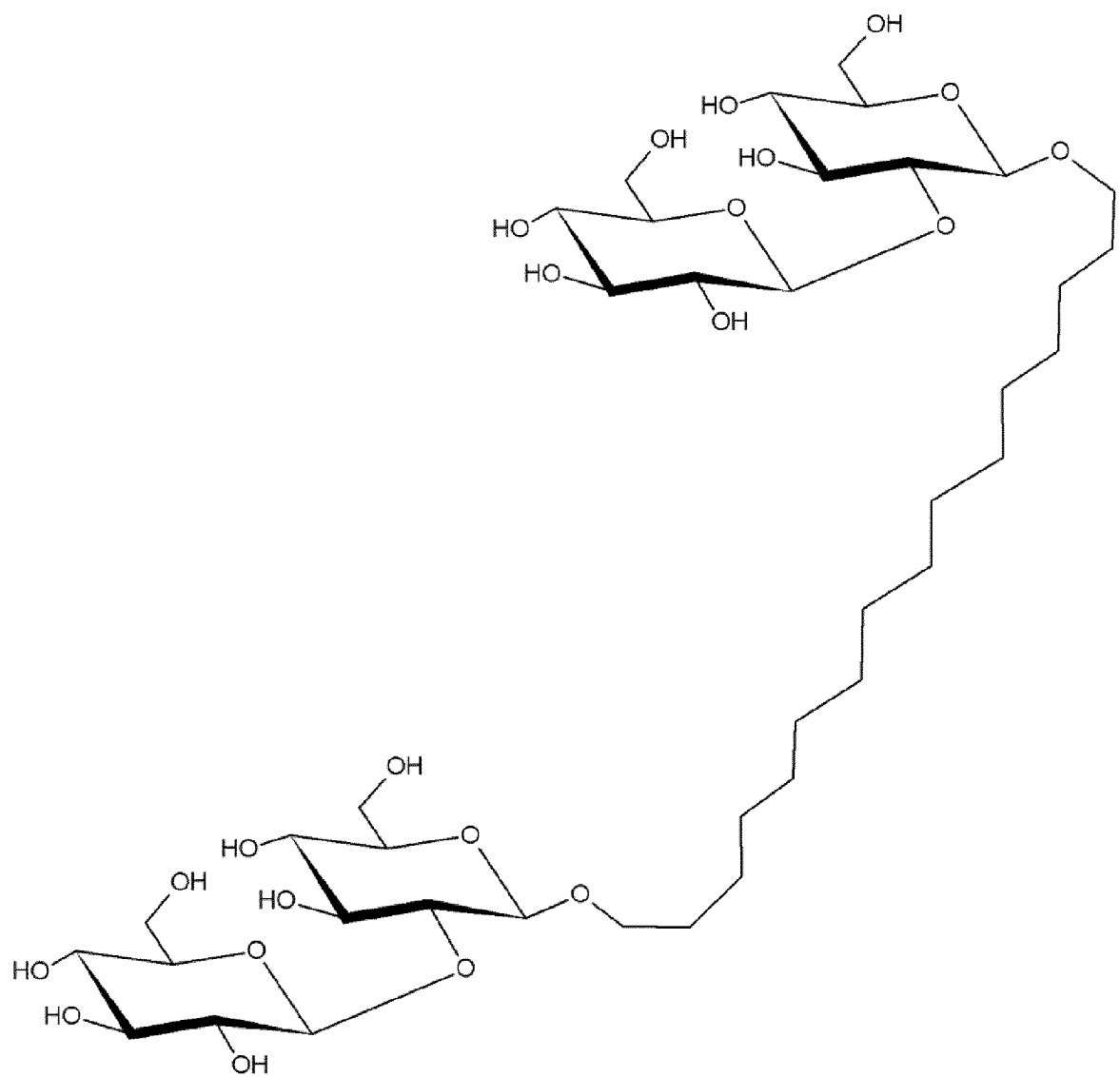
FIG. 15: Structure of a symmetric bolaform sophorolipid.

As described above and as depicted in FIG. 1, the hydrophobic spacer of the bolaform sophorolipids described in the previous examples is, on one side, linked to the hydrophilic moiety by the traditional glycosidic bond occurring in the native sophorolipid and, on the other side, by an ester bond. Hence, the molecules are not fully symmetric and, as explained above (and in Example 9), the ester bond is more prone to (alkaline) hydrolysis. Yet, by applying alternative hydrophobic substrates such as commercially available fatty alcohols, symmetric bolaform sophorolipids with increased resistance to chemical hydrolysis can be obtained (see, for example, FIG. 15).

The term "fatty alcohols" relates to primary long-chain alcohols, for example, 1-dodecanol, 1-tetradecanol or 1-octadecenol. The term "diol" refers to a molecule with two hydroxyl groups. Thus, this molecule may contain an alkyl chain and the hydroxyl groups are positioned at both ends of the chain. Non-limiting examples are 1-12 dodecanediol, 1-14 tetradecanediol, 1-16 hexadecanediol, 1-18 octadecanediol or 1-18, octadecanediol.

The disclosure thus also relates to a method of producing symmetric bolaamphiphilic glycolipids comprising:
providing a fungal strain comprising a dysfunctional acetyltransferase, or comprising a dysfunctional acetyltransferase and a dysfunctional lactonase, or comprising a dysfunctional acetyltransferase and a dysfunctional cytochrome P450 monooxygenase, or comprising a dysfunctional acetyltransferase, a dysfunctional lactonase and a dysfunctional cytochrome P450 monooxygenase, culturing the fungal strain using fatty alcohols and/or diols as a substrate in order to obtain a fermentation broth comprising a mixture of several types of glycolipids, and recovering the symmetric bolaamphiphilic glycolipids from the fermentation broth, wherein the symmetric bolaamphiphilic glycolipids are molecules having a hydrophobic spacer with hydrophilic glucose molecules at both ends of the spacer, wherein the hydrophilic glucose molecules are linked to both sides of the spacer by a glycosidic bond, and wherein the fungal strain is a yeast selected from the group consisting of *Starmerella (Candida) bombicola, Candida apicola, Candida batistae, Candida floricola, Candida riodocensis, Candida stellate, Candida kuoi, Candida* sp. NRRL Y-27208, *Rhodotorula bogoriensis* sp., *Wickerhamiella domericqiae* and a sophorolipid-producing strain of the *Starmerella* clade.

The latter fungal strains may thus, besides a dysfunctional acetyltransferase, also comprise a dysfunctional lactonase gene and/or an additional dysfunctional cytochrome P450 monooxygenase gene. An example of the latter monooxygenase gene is CYP52M1 (GenBank Accession number ACD75398.1).

This disclosure will now be illustrated by the following non-limiting examples.

EXAMPLES

Example 1

Production of Bolaform Sophorolipids Comprising Four Glucose Molecules by an Acetyltransferase-Negative Strain A *S. bombicola* strain knocked-out in the acetyltransferase gene responsible for acetylation of sophorolipids (GenBank accession number HQ670751) was derived from the parental *Starmerella bombicola* ATCC 22214 strain as described in Saerens et al. (2011b) and is referred to as *Starmerella bombicola* AT3. For sophorolipid production, the medium described by Lang et al. (2000) was used. 37.5 g/L rapeseed oil was added two days after inoculation. Yeast cultures were incubated at 30° C. and 200 rpm for a total time of 10 days.

Sophorolipid samples were extracted as follows: 3 mL of ethanol was added to 1 mL culture broth and shaken vigorously for 5 minutes. After centrifugation at 9,000 g for 5 minutes, the supernatant was collected. At the end of the incubation period, 3 volumes ethanol were added to the culture broth for total extraction of sophorolipids. Cell debris was removed by centrifugation at 1500 g for 10 minutes.

For further gravimetric analysis and total extraction of the glycolipids, the supernatant water-ethanol mixture was evaporated. Two volumes of ethanol were added to dissolve the sophorolipids and the residual hydrophobic carbon source. The mixture was filtrated to remove the water-soluble compounds and was evaporated again. One volume of water was added and set at pH 7, then 1 volume of hexane was added and, after vigorous shaking, the mixture was allowed to separate. The different fractions were collected, evaporated and the mass was determined. The hexane phase will contain residual oil, while the water phase contains the sophorolipids.

Samples were analyzed by HPLC and Evaporative Light Scattering Detection as described below.

Glucose concentration in the culture supernatant was determined by analysis with the 2700 Select Biochemistry Analyzer (YSI Inc.).

Colony forming units (CFU) were determined by plating decimal dilutions on agar plates with 10% glucose, 1% yeast extract and 0.1% urea that were incubated at 30° C. for three days.

Glycolipid samples were analyzed by HPLC on a Varian Prostar HPLC system using a CHROMOLITH® Performance RP-18e 100-4.6 mm column from Merck KGaA at 30° C. and Evaporative Light Scattering Detection (Alltech). A gradient of two eluents, a 0.5% acetic acid aqueous solution and acetonitrile, had to be used to separate the components. The gradient started at 5% acetonitrile and linearly increased to 95% in 40 minutes. The mixture was kept this way for 10 minutes and was then brought back to 5% acetonitrile in 5 minutes. A flow rate of 1 mL/minute was applied. In order to be able to compare and quantify the different samples, dilutions of a standard were analyzed in parallel.

Liquid chromatography mass spectrometry (LC-MS) analysis was performed on a Shimadzu LC10AD vp LC system with a Quattro LC MS detector from Waters, applying electron spray ionization (ESI). The detection range was set at m/z 200 to 1000 and the negative ion mode was applied. The same column and LC conditions as for the HPLC analysis were used.

Figure 3:
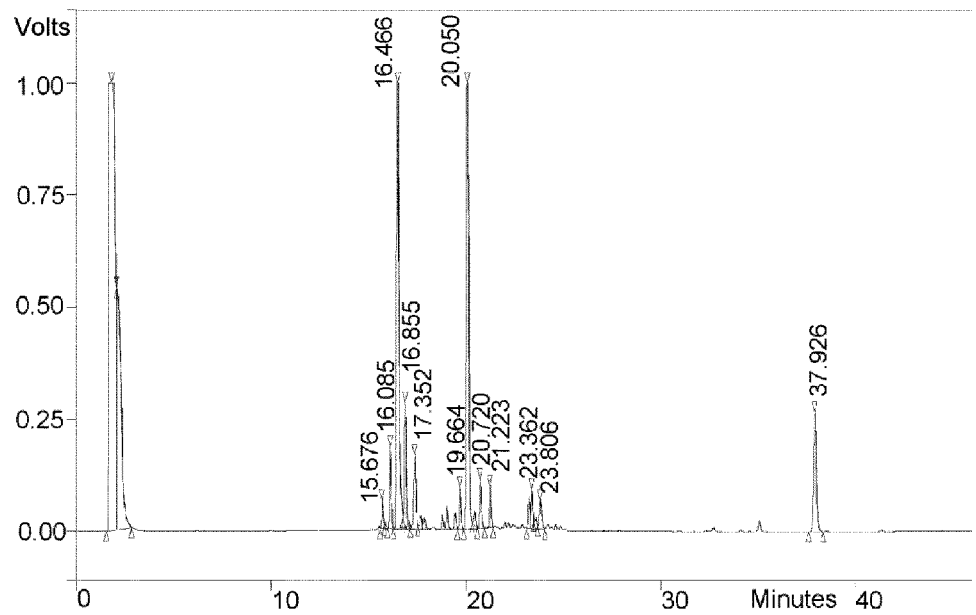
FIG. 3: HPLC-ELSD chromatogram of ethanol-extracted glycolipids produced by the acetyltransferase knock-out strain (Δat; single knock out). Compounds eluting between 18 and 24 minutes are derived from the standard, non-acetylated sophorolipids. Non-acetylated glucolipids containing four glucose molecules are detected between 15 and 18 minutes.

When glycolipids were obtained with the protocol as described above instead of with the commonly applied ethylacetate extraction method, unexpectedly, more hydrophilic compounds were detected by HPLC (FIG. 3). Indeed, compounds eluting between 18 and 24 minutes are derived from the standard, non-acetylated sophorolipids containing two glucose molecules, while several more hydrophilic compounds were detected between 15 and 18 minutes. These are non-acetylated glucolipids containing four glucose molecules as determined by LC-MS analysis. The fatty acid moiety of the mean component eluting at 16.466 minutes is oleic acid (C18:1), as confirmed by MS analysis (MW: 946 g/L). Peaks eluting just before this compound are derived from molecules with a saturated and mono-unsaturated C16 fatty acid tail (MW: 920 and 918 g/mol, respectively). The peak at 16.855 originates from the C18:1 compound with a terminal hydroxylation and the C18:0 harboring molecule elutes at 17.352 minutes (MW: 948 g/mol). The abundance of bolaform tetraglucolipids in the total mix represents about 50%.

Example 2

Production of Bolaform Sophorolipids Comprising Four Glucose Molecules by a Combined Acetyltransferase and Lactonase Negative Strain A strain, both knock-out in the acetyltransferase (GenBank accession number HQ670751) and lactonase gene, was created. First, a lactonase-negative strain was created as described in WO 2013/092421.

Next, the lactonase-negative strain was transformed by electroporation with the acetyltransferase knock-out cassette as described in WO 2012/080116 and Saerens et al., 2011b). Correct transformants were selected on YPD plates (10 g/L yeast extract, 20 g/L pepton, 20 g/L glucose and 20 g/L agar) containing 500 mg/L hygromycine and checked by yeast colony PCR with primer pairs KOATCtrl_F (CAGCAGAGACCATCTGCCTAGCAACTTC=SEQ ID NO:1) and GAPD-77SR (GCCACTGCCATTGGAGATTG=SEQ ID NO:2), and HygroInsertCheckFor (TTCGACAGCGTCTCCGACCTGAT=SEQ ID NO:3) and MDRSeq4 (TGGTCTGGCCCTGAGTCTGAAG=SEQ ID NO:4) for, respectively, correct 5' and 3' integration.

Culture conditions at shake flask scale were identical as described for Example 1, as well as sampling, HPLC and LC-MS analysis of glycolipids.

Three correct transformants were selected and sophorolipid production was evaluated with the wild-type *S. bombicola* ATCC 22214 as a reference. Throughout the whole incubation and production period, CFUs were similar to the wild-type, and glucose consumption was similar during the first part of the production period, but became slightly slower during the last four days. Yet, total sophorolipid yields were comparable to the wild-type and values between 20 and 30 g/L were obtained.

Figure 4:
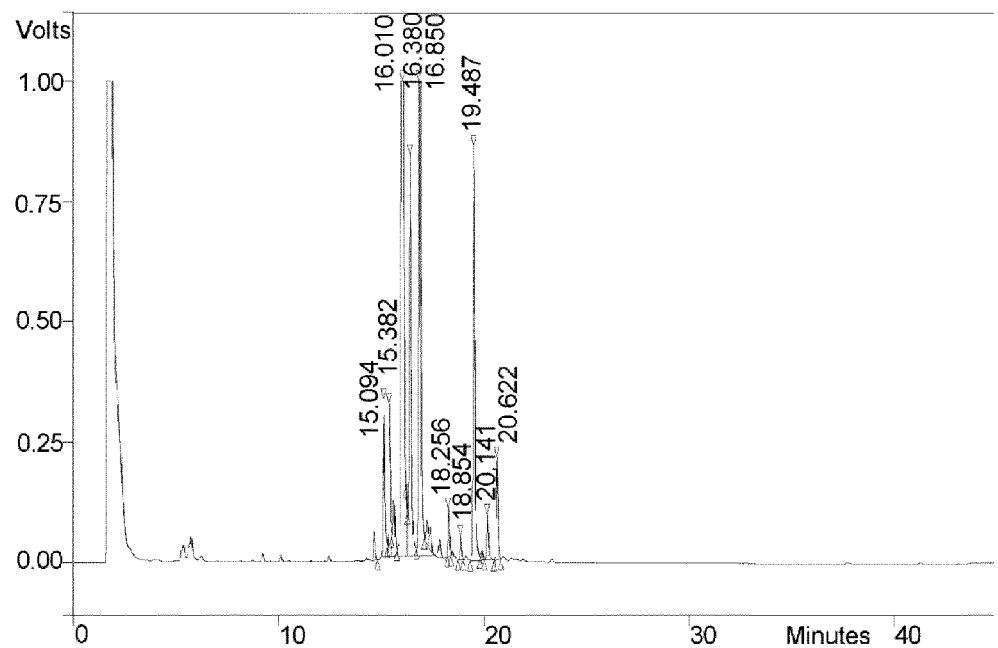
FIG. 4: HPLC-ELSD chromatogram of ethanol-extracted glycolipids produced by the acetyltransferase- and lactonase-negative strain (ΔatΔlac; double knock out). Compounds eluting between 18 and 21 minutes are derived from the standard, non-acetylated acidic sophorolipids. Non-acetylated glucolipids containing four glucose molecules are detected between 15 and 18 minutes.

Again, HPLC analysis demonstrated presence of both glycolipids comprising four and two (conventional sophorolipids) glucose molecules (FIG. 4). The later ones elute between 18 and 21 minutes and are non-acetylated acidic sophorolipids. The new compounds are more hydrophilic and are detected between 15 and 18 minutes. These are non-acetylated bolaform glucolipids containing four glucose molecules as determined by LC-MS analysis. The fatty acid moiety of the mean component eluting at 16.010 minutes is oleic acid (C18:1), as confirmed by MS analysis (MW: 946 g/mol). Peaks eluting just before this compound are derived from molecules with a saturated and mono-unsaturated C16 fatty acid tail (MW: 920 and 918 g/mol, respectively). The peak at 16.380 originates from the C18:1 compound with a terminal hydroxylation and the C18:0 harboring molecule elutes at 16.850 minutes (MW: 948 g/mol). The new molecules represent over 50% of the glycolipids mixture, based on the HPCL-ELSD chromatograms.

Example 3

Glucosyltransferase Enzyme Tests

*S. bombicola* wild-type, the ugtA1 deletion mutant A113 (knocked out in the first glucosyltransferases: GenBank accession number HM440973; Saerens et al., 2010a), the ugtB1 deletion mutant B11 (knocked out in the second glucosyltransferases: GenBank accession number HM440974; Saerens et al., 2010c) and the acetyltransferase deletion mutant were grown overnight in 5 mL 3C medium (100 g/L glucose, 10 g/L yeast extract and 1 g/L urea) at 30° C. and 200 rpm. The culture was used to inoculate 20 mL 3C medium and was incubated the same way for about 60 hours. Cells were harvested by centrifugation at 4000 rpm for 10 minutes and washed with 20 ml distilled water. The pellet was suspended in a 50 mM potassium phosphate lysis buffer pH 8.5 containing 5% glycerol, 0.5 mM $MgCl_2$, 0.5 mM DTT and 1 mM PMSF to $OD_600$ of 100. An equal volume of acid-washed glass beads (150-212 µm diameter, Sigma) were added and cells were disrupted by vortexing during 15 minutes with 30-second intervals on ice. Soluble protein fractions were used for enzyme assays after centrifugation of the crude lysate at 4000 rpm for 10 minutes. Protein concentration in the lysate was determined by means of the BCA™ Protein Assay Kit (Pierce). Protein solutions were stored at 4° C.

UDP-glucose and sophorose-monohydrate was obtained from Sigma, 17-hydroxyl-octadecenoic acid and glucolipid were obtained from sophorolipids as described before (Saerens et al., 2009). Acidic sophorolipids were obtained after alkaline treatment of a standard sophorolipid mixture (Rau et al., 1999). All substrate solutions were prepared freshly in 50 mM potassium-phosphate buffer, pH 8.5.

Enzyme assays contained 2 mM UDP-glucose, 2 mM acceptor and 200 µl fresh protein solution in a total volume of 500 µl. No UDP-glucose was added to the blank reactions and positive controls were conducted with the described substrates 17-hydroxyl-octadecenoic acid and glucolipids for the ugtB1 and ugtA1 mutants, respectively. The reactions were incubated at 30° C. for 1 hour (positive controls), or 4 or 24 hours and were stopped by incubation at 95° C. for 5 minutes. After 1 minute centrifugation at 13000 rpm, the supernatants were collected and analyzed.

HPLC-ELSD and LC-MS analysis were conducted as described for Example 1. Further characterization was performed by a MALDI 4800 Proteomics Analyzer, MS-MS detection in positive mode. The sample was diluted 5× in 0.1% HCOOH—1/1 a-cyanohydroxycinnamic acid matrix or a 2× dilution was made in 0.1% HCOOH/50% ACN 1/1 a-cyanohydroxycinnamic acid matrix for detection of compounds harboring more than four glucose molecules.

Figure 5:
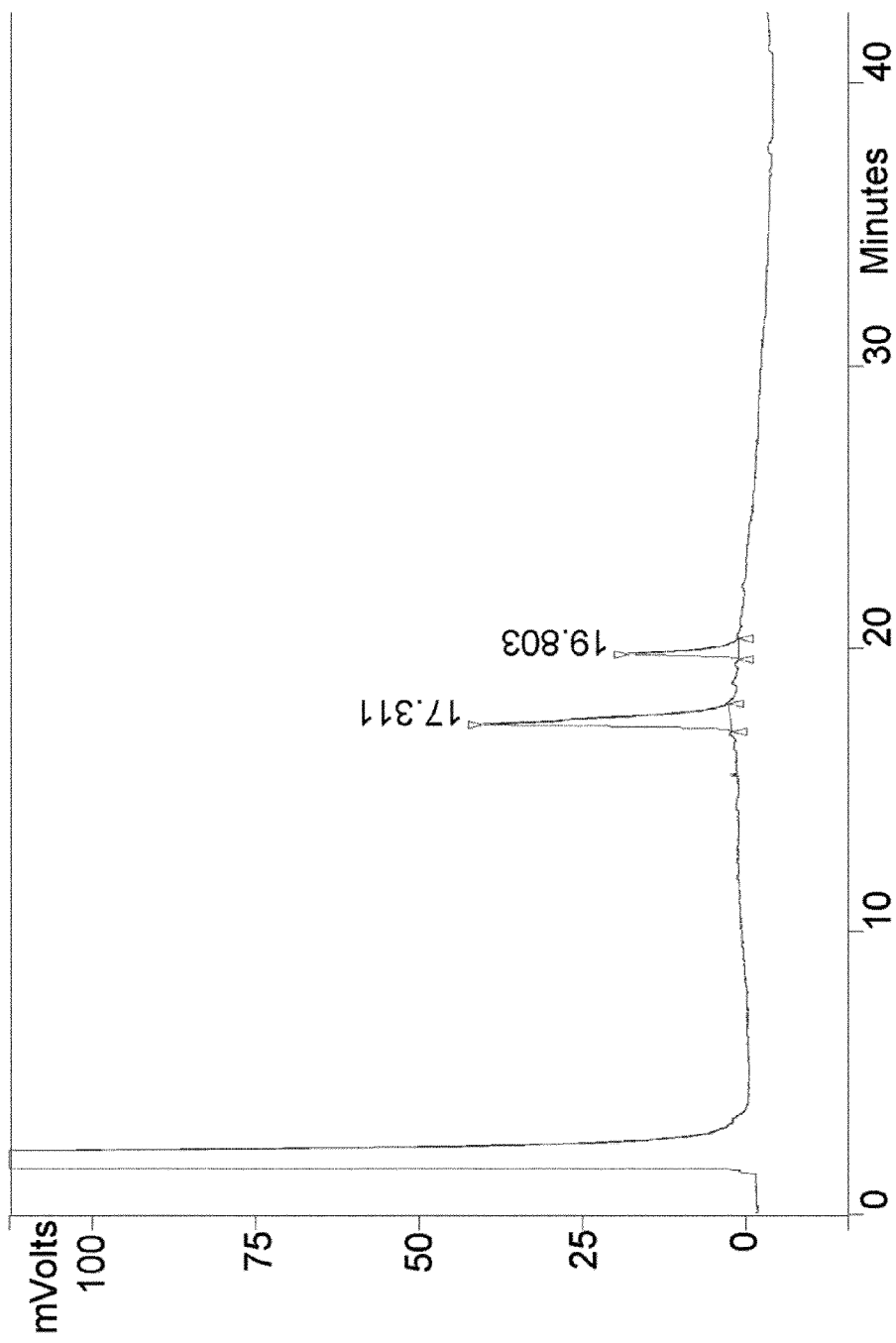
FIG. 5: HPLC-ELSD chromatogram of an enzyme assay with B11 lysate and acidic sophorolipids as substrate (detected at 19.803 minutes), incubated for 24 hours. The product elutes at 17.311 minutes and consists of a molecule with three glucose moieties, indicating that the first glucosyltransferase is able to transfer an additional glucose.

The A113 and B11 strains are, respectively, knocked out in the first and second sophorolipid UDP-glucosyltransferase. Enzyme assays with A113 lysates will thus provide information on the second glucosyltransferase activity while tests with B11 lysates will give info on the first glucosyltransferase reaction. Upon incubations with acidic, non-acetylated sophorolipids, no activity was detected for the A113 mutant, while the acid sophorolipids were converted by the B11 lysate to a compound harboring three glucose molecules as confirmed by LS-MS. FIG. 5 depicts the substrate (non-acetylated acidic sophorolipids) and the product (molecules with three instead of two glucose molecules) eluting at 19.803 and 17.311 minutes, respectively. Incubations with lysates from the wild-type so having both the glucosyltransferase activities and non-acetylated acidic sophorolipids resulted in the formation of compounds with four glucose molecules as detected for the cultivations in Examples 1 and 2. Furthermore, molecules with six glucose molecules and two alkyl chains (three sophorose units) were detected by MALDI-$MS^2$ analysis and where present both as $[M+Na]^+$ and $[M+K]^+$ ions.

The same findings were obtained for lysates from the acetyltransferase knock-out strain.

These findings prove that the first glucosyltransferase adds the third glucose molecule, while the second one adds the fourth one. Therefore, just as for standard sophorolipid production, the enzymes act in a stepwise manner.

No activity was detected for sophorose as acceptor.

Example 4

Confirmation of the Chemical Structure by NMR

The major compound of the sophorolipid mixture as described in Example 2, a non-acetylated sophorolipids molecule comprising four glucose molecules and harboring a C18:1 fatty acid tail, was isolated from the total mix by repetitive and combined fraction collection after separation on the HPLC column as described under 1.1.3. Solvent was removed by vacuum evaporation.

All NMR spectra were measured on an AVANCE® II Bruker Spectrometer operating at a 1H frequency of 700 MHz and equipped with a $^1H/^{13}C/^{15}N$ TXI-z probe. The dry sample (±4-5 mg) was dissolved in 544.5 μl $D_2O$, together with a 5.5-μl DSS in $D_2O$ solution (550 μl in total), in order to obtain a concentration of around 9.6 mM with 0.05 mM DSS. All spectra were referenced to the DSS signal at 0.00 (Gheysen et al., 2008) ppm for the $^1H$ frequency. The spectra recorded on the sample included 1D $^1H$ (quantitative), 2D$^1H$-{$^1H$} COSY, $^1H$-{$^1H$} TOCSY (100 ms spinlock), $^1H$-{$^1H$} Off-Resonance ROESY (300 ms spinlock), $^1H$-{$^{13}C$} HSQC, $^1H$-{$^{13}C$} HSQC-TOCSY (100 ms spinlock) and $^1H$-{$^{13}C$} HMBC with a 5-Hz long-range coupling constant. All spectra were processed using TOPSPIN 3.2 p11.

Since the sample is dissolved in $D_2O$, all the exchangeable protons will exchange with deuterium and, hence, will not be visible in the $^1H$ spectra. This limits the number of protons that have to be assigned to 60. Although the sample is dissolved in $D_2O$, a considerable amount of $H_2O$ remains and at 25° C., its signal overlaps with some of the anomeric protons. These anomeric protons are of high importance in the assignment, since they are situated in a relatively overlap-free region and correlate with the other protons in each sugar ring. By recording all the spectra at 15° C., the $H_2O$ signal shifts to a higher chemical shift value, hereby resolving the overlap.

Due to the low sample quantity, no $^{13}C$ spectra are recorded; nevertheless, this molecule only contains one quaternary carbon atom, meaning all the other carbon atoms can be assigned using the HSQC spectrum. The quaternary carbon atom itself will be assigned using the HMBC spectrum.

Figure 6:
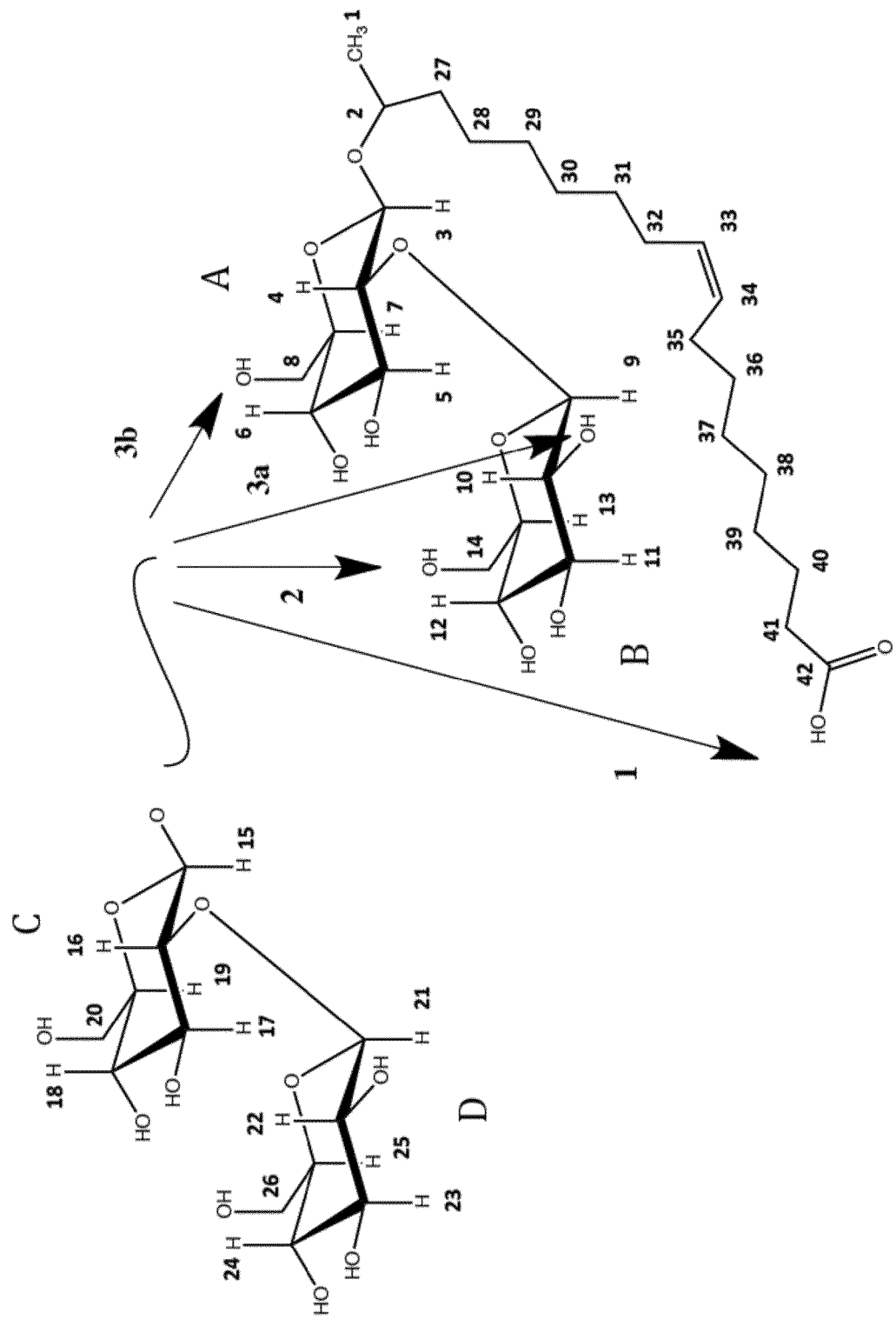
FIG. 6: Hypothetical connections of the additional sophorose unit.

The novel molecules described by Price et al. (2011), were only examined by LC-MS and the structure was suggested based merely on the molecular weight. However, linkage of an additional sophorose unit could occur at various positions (FIG. 6) and even the fact that the additional sugars should form a sophorose has not been proven. Alkaline hydrolysis of the sample obtained in Example 3 already suggested coupling by the carboxylic end as the molecule was disrupted and normal acidic sophorolipids were formed, an event that could only happen if an ester bond was present such as suggested in FIG. 6, option 1. The NMR results are summarized in Tables 2 and 3 and indeed confirm coupling to the carboxylic acid as demonstrated by the highest shift in the HMBC to a carbon atom at 175.26 ppm. The data confirm the sophorose structure as well (β 1-2 connection) as demonstrated by the somewhat higher shift for C16 and C4.

TABLE 2

Overview $^1H$ chemical shift signals and assignments $^1H$ signals

| δ 1H (ppm) | multiplicity | Integral | # protons | Annotation |
|---|---|---|---|---|
| 1.25 | doublet | 3.00 | 3 | 1 |
| 1.34 | broad singlet | 14.68 | 15 | 29, 30, 31, 34, 36, 37, 38, 39 |
| 1.45 | broad singlet | 2.00 | 1 | 28 |
| 1.46 | broad singlet | 2.00 | 1 | 27 |
| 1.59 | broad singlet | 3.19 | 1 | 27 |
| 1.65 | broad singlet | 3.19 | 2 | 40 |
| 2.06 | singlet | 8.58 | 4 | 35, 32 |
| 2.49 | triplet | 2.01 | 2 | 41 |

TABLE 2-continued

Overview $^1H$ chemical shift signals and assignments $^1H$ signals

| δ 1H (ppm) | multiplicity | Integral | # protons | Annotation |
|---|---|---|---|---|
| 3.27 | multiplet | 2.90 | 1 | 22 |
| 3.29 | 10 | 2.90 | 1 | 10 |
| 3.32 | 12 | 2.90 | 1 | 12 |
| 3.38 | doublet | 1.06 | 1 | 24 |
| 3.41 | broad multiplet | 3.81 | 1 | 25 |
| 3.42 | broad multiplet | 3.81 | 1 | 7 |
| 3.42 | broad multiplet | 3.81 | 1 | 6 |
| 3.42 | broad multiplet | 3.81 | 1 | 13 |
| 3.50 | broad triplet | 3.00 | 1 | 18 |
| 3.50 | broad triplet | 3.00 | 1 | 11 |
| 3.50 | broad triplet | 3.00 | 1 | 23 |
| 3.55 | triplet | 2.10 | 1 | 4 |
| 3.58 | broad multiplet | 2.10 | 1 | 19 |
| 3.67 | multiplet | 6.89 | 1 | 5 |
| 3.69 | multiplet | 6.89 | 1 | 14 |
| 3.72 | multiplet | 6.89 | 1 | 26 |
| 3.73 | multiplet | 6.89 | 1 | 8 |
| 3.73 | multiplet | 6.89 | 1 | 20 |
| 3.75 | multiplet | 6.89 | 1 | 16 |
| 3.77 | multiplet | 6.89 | 1 | 17 |
| 3.86 | multiplet | 5.01 | 1 | 26 |
| 3.88 | multiplet | 5.01 | 1 | 20 |
| 3.88 | multiplet | 5.01 | 1 | 8 |
| 3.88 | multiplet | 5.01 | 1 | 2 |
| 3.91 | multiplet | 5.01 | 1 | 14 |
| 4.58 | doublet | 0.97 | 1 | 3 |
| 4.70 | doublet | 0.92 | 1 | 21 |
| 4.79 | doublet | 0.97 | 1 | 9 |
| 5.45 | singlet | 2.03 | 2 | 34, 33 |
| 5.70 | doublet | 1.06 | 1 | 15 |
| | Total: | | 60 | |

TABLE 3

Overview $^{13}C$ chemical shift signals and assignments.

| δ 13C (ppm) | Type of C | # carbons | Annotation |
|---|---|---|---|
| 21.53 | CH3 | 1 | 1 |
| 24.72 | CH2 | 1 | 40 |
| 25.24 | CH2 | 1 | 28 |
| 25.27 | | | |
| 27.46 | CH2 | 2 | 35, 32 |
| 29.59 | CH2 | 7 | 29, 30, 31, 36, 37, 38, 39 |
| 34.54 | CH2 | 1 | 41 |
| 36.70 | CH2 | 1 | 27 |
| 36.70 | | | |
| 61.02 | CH2 | 1 | 20 |
| 61.03 | | | |
| 61.30 | CH2 | 1 | 8 |
| 61.30 | | | |
| 61.55 | CH2 | 1 | 26 |
| 61.56 | | | |
| 62.01 | CH2 | 1 | 14 |
| 62.02 | | | |
| 69.60 | CH | 1 | 18 |
| 69.97 | CH | 1 | 6 |
| 70.24 | CH | 1 | 24 |
| 70.62 | CH | 1 | 12 |
| 74.48 | CH | 1 | 22 |
| 74.71 | CH | 1 | 10 |
| 76.10 | CH | 1 | 23 |
| 76.17 | CH | 1 | 17 |
| 76.29 | CH | 1 | 11 |
| 76.35 | CH | 1 | 7 |
| 76.88 | CH | 1 | 25 |
| 76.97 | CH | 1 | 13 |
| 77.14 | CH | 1 | 5 |
| 77.26 | CH | 1 | 19 |
| 79.36 | CH | 1 | 2 |

TABLE 3-continued

Overview $^{13}$C chemical shift signals and assignments.

| δ 13C (ppm) | Type of C | # carbons | Annotation |
|---|---|---|---|
| 80.18 | CH | 1 | 4 |
| 80.67 | CH | 1 | 16 |
| 93.33 | CH (anomeric) | 1 | 15 |
| 101.56 | CH (anomeric) | 1 | 3 |
| 103.14 | CH (anomeric) | 1 | 9 |
| 103.78 | CH (anomeric) | 1 | 21 |
| 131.27 | CH (alkene) | 2 | 34, 33 |
| 175.26 | Cq (ester) | 1 | 42 |
| | Total: | 42 | |

Example 5

Creation of Bolaform Sophorolipids with One Glucose Molecule at Each Site

A Δugtb1 Δat strain was created by transforming the B11 Δugtb1 strain (a strain knocked out in the second glucosyltransferase; Saerens et al., 2011c and WO 2011/154523) with the acetyltransferase knock-out cassette as described in WO 2012/080116 and Saerens et al., 2011b. Correct transformants were selected on YPD plates (10 g/L yeast extract, 20 g/L pepton, 20 g/L glucose and 20 g/L agar) containing 500 mg/L hygromycine and checked by yeast colony PCR with primers, the pairs as described under Example 2.

Culture conditions, sampling and analysis are identical as described for Example 1.

The glycolipids produced by the B11 strain are glucolipids (only one glucose molecule attached to a hydroxylated fatty acid), which harbor one acetylation or none (Saerens et al., 2011c). By additional introduction of the acetyltransferase knock-out, in this way creating a Δugtb1 Δat strain, non-acetylated glucolipids are produced, as well as glucolipids with one additional glucose at the free carboxylic end as depicted in FIG. 7. Three genetically identical mutants were compared to the wild-type strain. Glycolipid yield for this strain was less as compared to the wild-type, as can be expected from the observed slower glucose consumption, while CFU numbers were more or less similar. HPLC analysis did not reveal any conventional sophorolipid peaks. Yet, some small new peaks were observed. That is why LC-MS analysis was performed. This revealed the presence of non-acetylated glucolipids in the medium with a mass of 460. The expected bola structure (FIG. 7) has a molecular mass of 622 as detected by MS. These new structures make up about 10% of the total glycolipid content.

Example 6

Selective Production of at Least 85% Bolaform Sophorolipids Comprising Four Glucose Molecules by Performing a Fed Batch Fermentation The production as described under Example 2 still comprised the production of wild-type sophorolipids in a mixture with the new molecules, which is unwanted. A fed batch fermentation process was thus developed to eliminate the formation of wild-type sophorolipids as much as possible.

Figure 8:
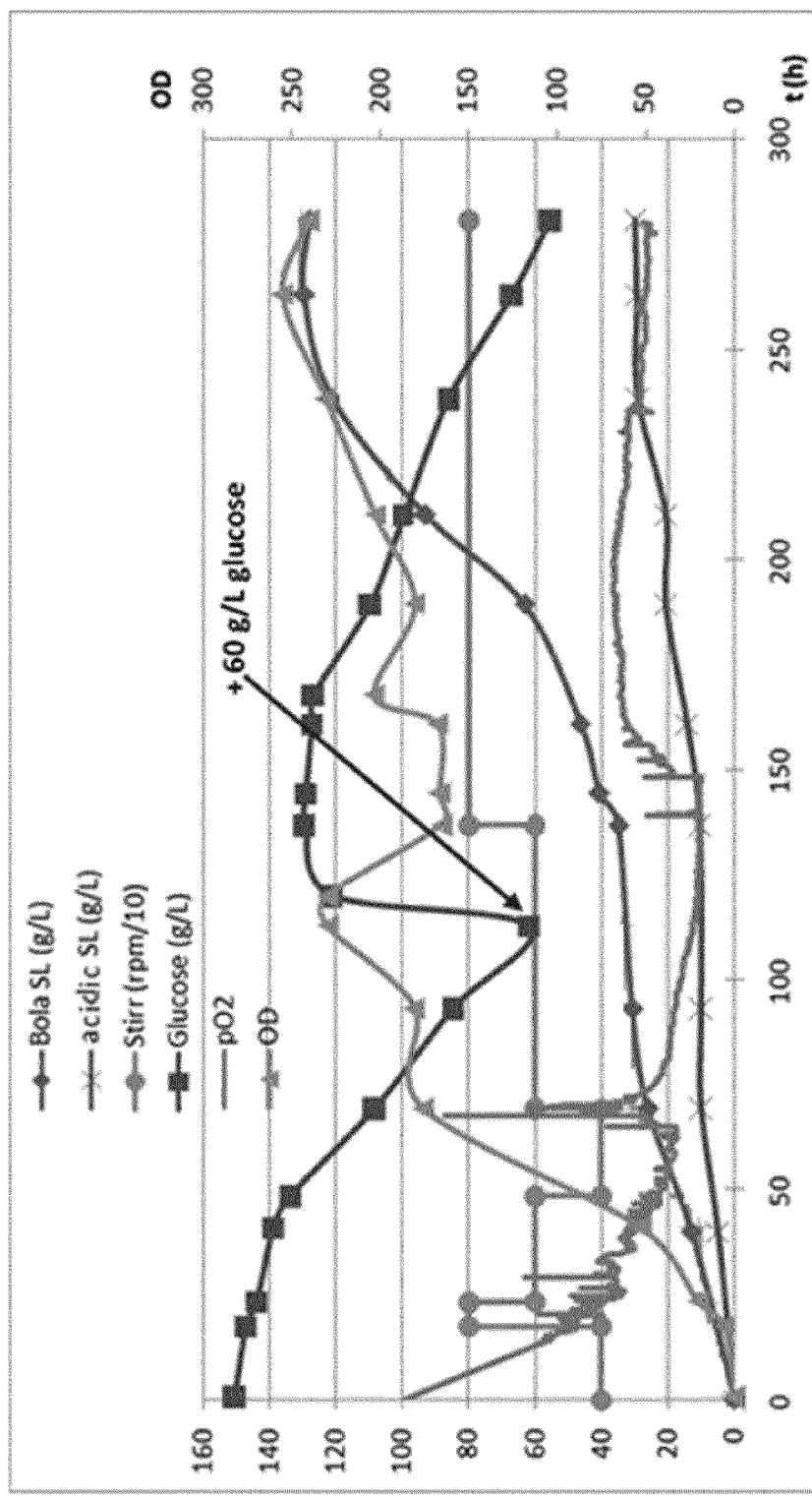
FIG. 8: Parameters of a fed batch fermentation with the ΔatΔlac strain at the 3 L scale (2 L working volume) with a productivity 0.46 g/L/h and a final percentage of bolaform sophorolipids of 85% (and 15% acidic sophorolipids).

Fermentations were first run at the 3-liter scale using the Biostat B 884032/6 reactor (B. Braum) with a working volume of 1.5 liters. An adapted version of the medium described by Lang (2000) with a glucose concentration of 150 g/L instead of 120 g/L was used for both the precultures and the reactor experiments and will be referred to as the "production medium." The seeding train consisted of two subsequent precultures (5 mL and 100 mL), which were cultivated (30° C., 200 rpm) between 48 and 72 hours. The 5 mL preculture was derived from a single colony of the ΔatΔlac strain, picked up from a 3C plate (100 g/L glucose, 10 g/L yeast extract and 1 g/L urea) and was inoculated into 100 mL of the production medium in a 500-mL shake flask. The latter was subsequently used for the inoculation of the bioreactor, which contained 1.1 liter of the production medium. Rapeseed oil was used as the hydrophobic substrate and was added in a concentration of 8.5 g/L after inoculation of the bioreactor. After that, daily portions of 5 grams of rapeseed oil were added to the bioreactor. The pH of the broth was kept at 4 using a concentrated (5N) NaOH solution. Stirring rate was adjusted to control the pO2 and the maximum stirring rate was 800 rpm. Daily samples were taken to evaluate the production of biosurfactant (bola sophorolipids and acidic sophorolipids) and residual glucose in the vessel. Glucose measurements were performed by using the ACCU-CHEK® Sensor Comfort blood glucose device (Roche). When the glucose dropped to 60 g/L, an additional shot of glucose (60 g/L) was added to the bioreactor (see FIG. 8). The OD of the samples was determined by using the JASCO® V-630 Bio spectrophotometer (600 nm). Samples were diluted with physiological solution (9.5% NaCl) to stay in the linear range of the spectrophotometer (0.1-1). The other fermentation parameters were followed up using the MFCS V2.1 software. An overview of these parameters is depicted in FIG. 8. The sophorolipid concentrations were calculated based on the generation of a dilution series of pure bolaform sophorolipids obtained as described under Example 7 and pure acidic sophorolipids obtained by alkaline hydrolysis of wild-type sophorolipids and analysis of these samples on HPLC-ELSD. After the determination of the relation between concentration and peak area, the actual concentrations in the fermentations could be calculated. This experiment was stopped after 275 hours and a final titer of 128 g/L bola sophorolipids being 85% of the total biosurfactant quantity was obtained. The residual 15% consisted of unwanted acidic sophorolipids.

Figure 9:
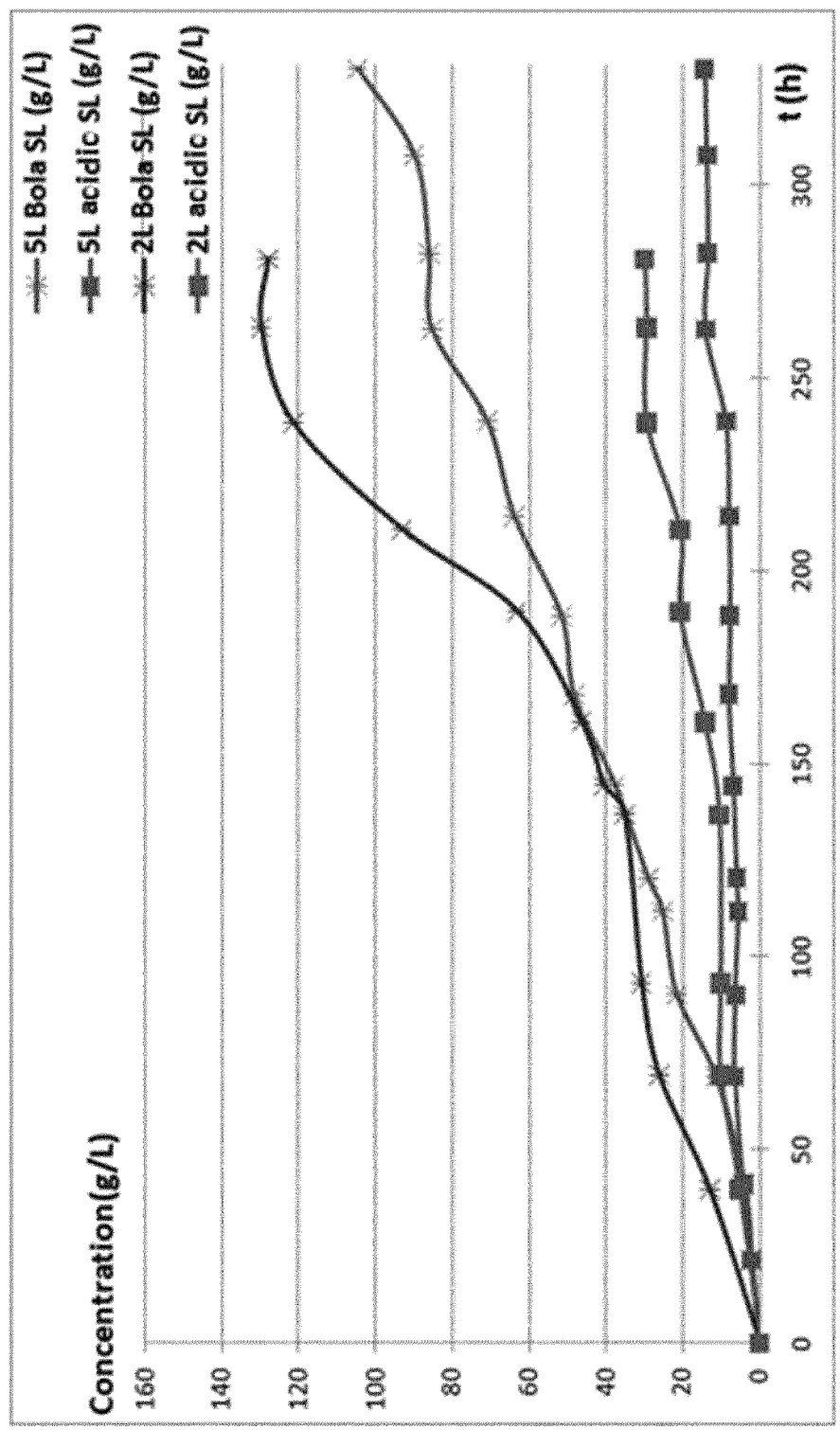
FIG. 9: Comparison of the bioreactor experiments at the 3 L (2 L working volume) and 7 L (5 L working volume) scale in terms of production of Bola sophorolipids and acidic sophorolipids throughout the bioreactor experiments.

The results were confirmed by repeating the experiment at the 7-liter scale (5-liter working volume) using the BIOSTAT® B Plus MFCS/win IFB RS-422 and fermentation parameters were followed up using the MFCS V2.1 software. The final titer of this fermentation added up to 105 g/L Bola sophorolipids, with only 14 g/L of unwanted acidic sophorolipids, thus representing 88% of bolaform sophorolipids of the total biosurfactant amount. The volumetric productivity equaled 0.32 g/L/h. In FIG. 9, a comparison between the production of these two experiments is given.

Example 7

Figure 10:
FIG. 10: Purified bolaform sophorolipids after ultra- and diafiltration followed by a final lyophilization step.

Purification of the Bolaform Sophorolipids Using Sequential Ultrafiltrations A purification method was developed by making use of sequential ultrafiltrations. The ultrafiltration experiments were all performed using the AMICON® 8200 filter cell and regenerated cellulose membranes with a cut off of 5 and 30 kDa (Millipore). The filter cell was placed on a magnetic stirrer to avoid clogging of the membranes and $N_2$ gas was used with a maximum pressure of 50 psi. The cell-free fermentation broth was first subjected to ultrafiltration using a 30-kDa membrane. At unchanged pH (4.21), almost all the bolaform sophorolipids (98%) were passing through this membrane, which resulted in the removal of contaminant proteins (up to 28% removal of total protein content) and polysaccharides or other cell remains larger than 30 kDa. Changing the pH influenced the retention of the bolaform sophorolipids: the higher the values (up to 6), the higher the retention. The retentate was washed with distilled water to get as much bolaform sophorolipids in the filtrates as possible. The resulting filtrates were subsequently subjected to a second ultrafiltration step using a 5-kDa cut off membrane, which retained 99.74% of the bolaform sophorolipids. The resulting retentate was subsequently washed with distilled water to eliminate small contaminants such as salts, sugars, peptides, etc., from the concentrated sophorolipid retentate. The washing also resulted in the removal of yellow/brown pigments from the retentate. The resulting retentate was subsequently frozen at −80° C. (24 hours) followed by lyophilization using the lyophilizator-type Alfa 1-4 5 (Christ Martin) until all remaining water was removed. The final product consisted of a dry white powder of the purified bolaform sophorolipids (FIG. 10).

Example 8

Determination of Characteristics of Bolaform Sophorolipids

Figure 11:
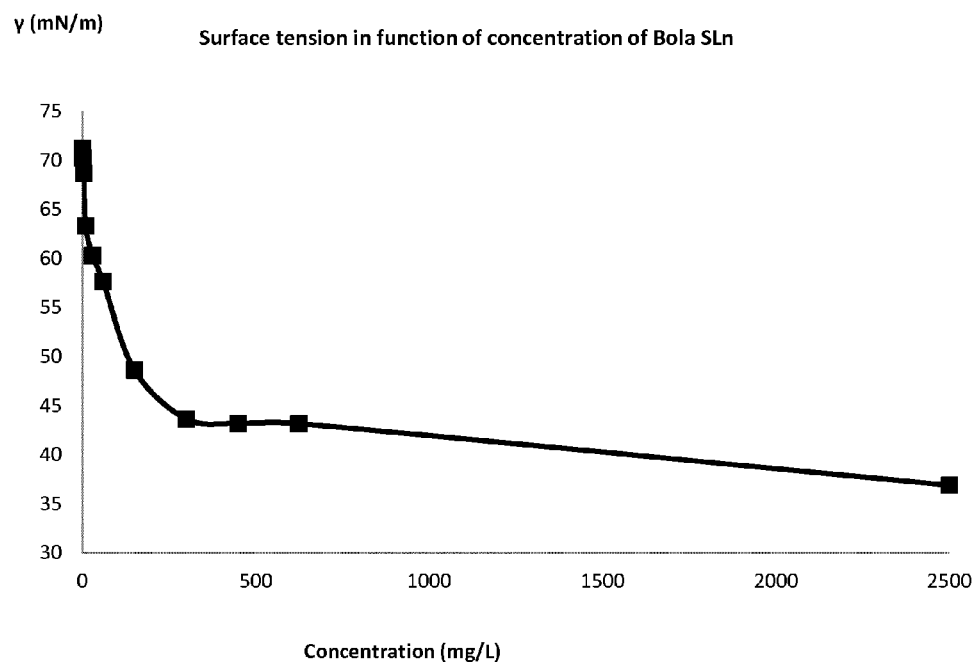
FIG. 11: Surface tension of the bolaform sophorolipids in function of the concentration thereof.

After the pure product was obtained (Example 8), certain specifications of the new products were determined to assess the stability and specific characteristics of these new molecules. The pH stability was determined by using HCl or NaOH to adjust the pH of the samples and subsequently analyze the stability of the molecules at a range of pH conditions by taking samples and analyzing these by HPLC-ELSD. The same was done for temperature. The critical micelle concentration (CMC) was determined by measuring the surface tension of a dilution series of purified bolaform sophorolipids. The surface tension was determined using the Wilhelmy plate method and the results are depicted in FIG. 11. Furthermore, dynamic light scattering (DLS) experiments were performed and these resulted in the prediction of special supramolecular assembly behavior of these molecules, which was already predicted by the results of the ultrafiltration experiments. A summary of the obtained results is given in Table 4.

TABLE 4

Specifications for the purified bolaform sophorolipids

| | |
|---|---|
| Product form (FIG. 10): | White dry powder |
| pH stability (22° C., 100 hours): | 2-6.5 |
| Temperature stability: | −80° C.-40° C. |
| CMC (22° C.): | 228 mg/L |
| Surface tension (@ CMC): | 36.4 mN/m |
| Special properties: | Supramolecular assembly |

Example 9

Figure 12:
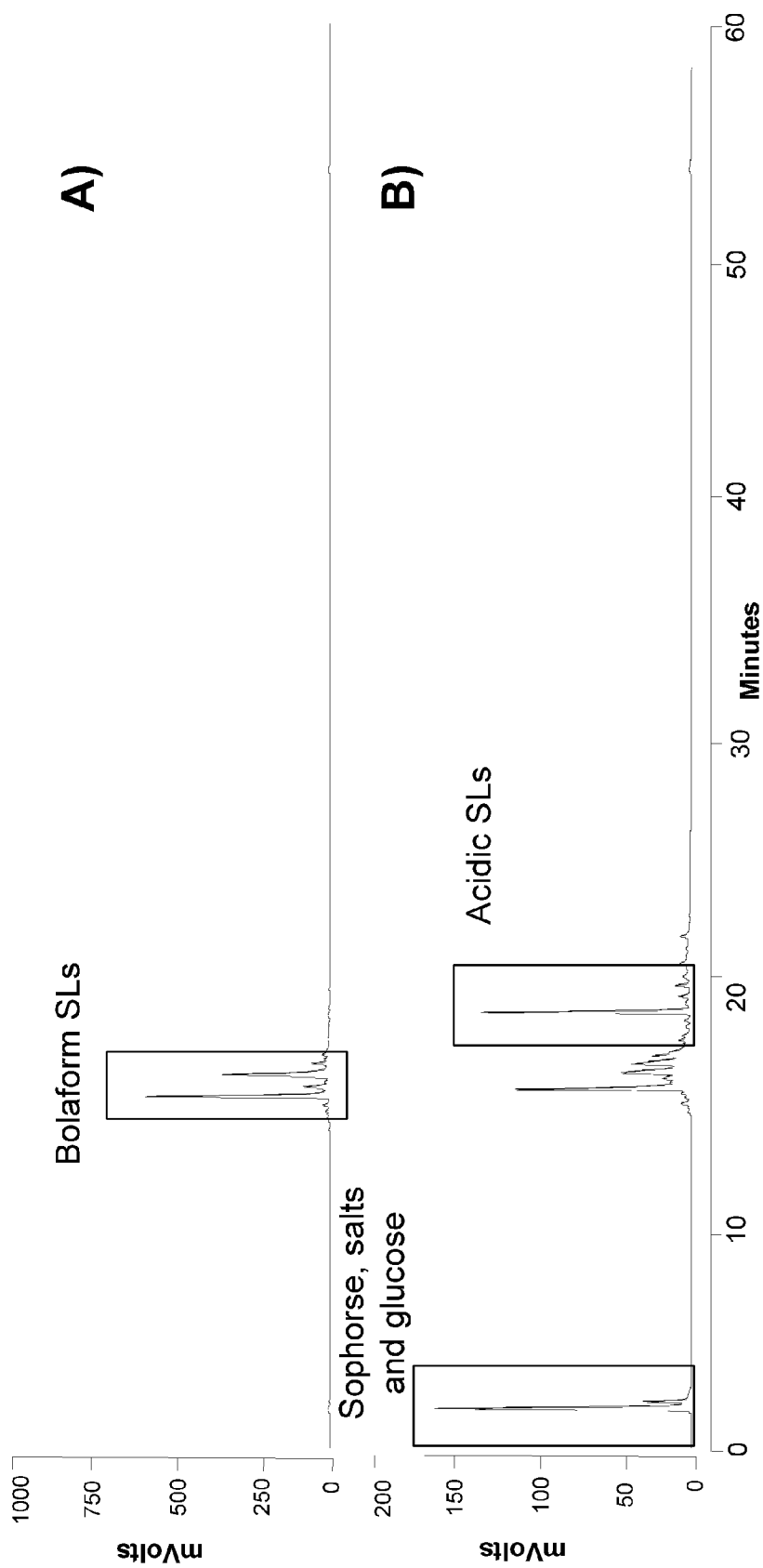
FIG. 12: Alkaline hydrolysis (pH 9) of bolaform sophorolipids after 3 hours at room temperature (Row B) and consisting of identical incubation, but at unchanged pH (Row A). Samples were brought back to the original pH to stop the hydrolysis reaction and then analyzed on HPLC-ELSD.
Figure 13:
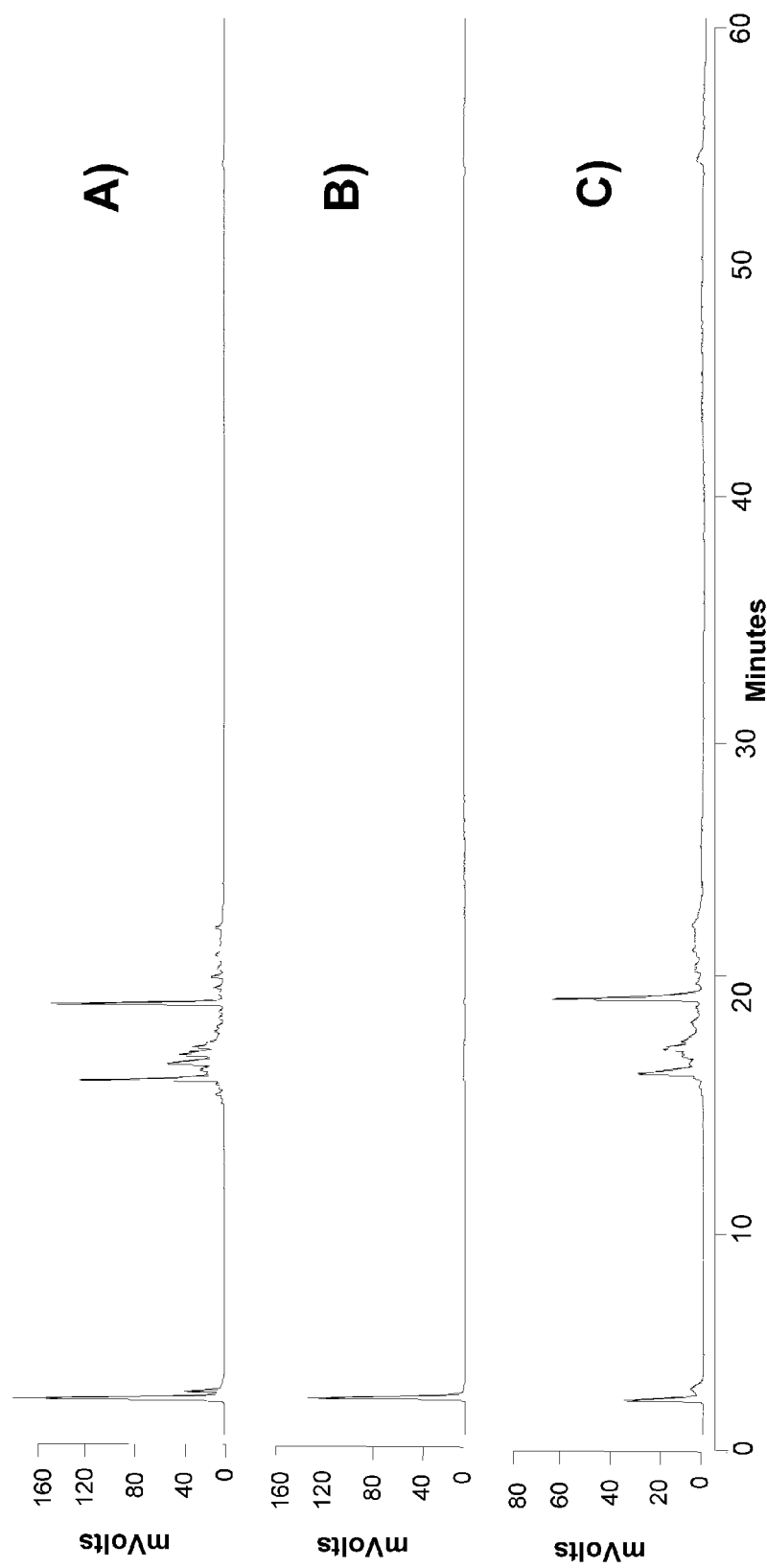
FIG. 13: HPLC-ELSD analysis of samples taken after ultrafiltration on a sample subjected to alkaline hydrolysis of bolaform sophorolipids. Row A) sample as it was before ultrafiltration, Row B) filtrate after one filtration step using a 1-kDa cut off, and Row C) the retentate thereof.
Figure 14:
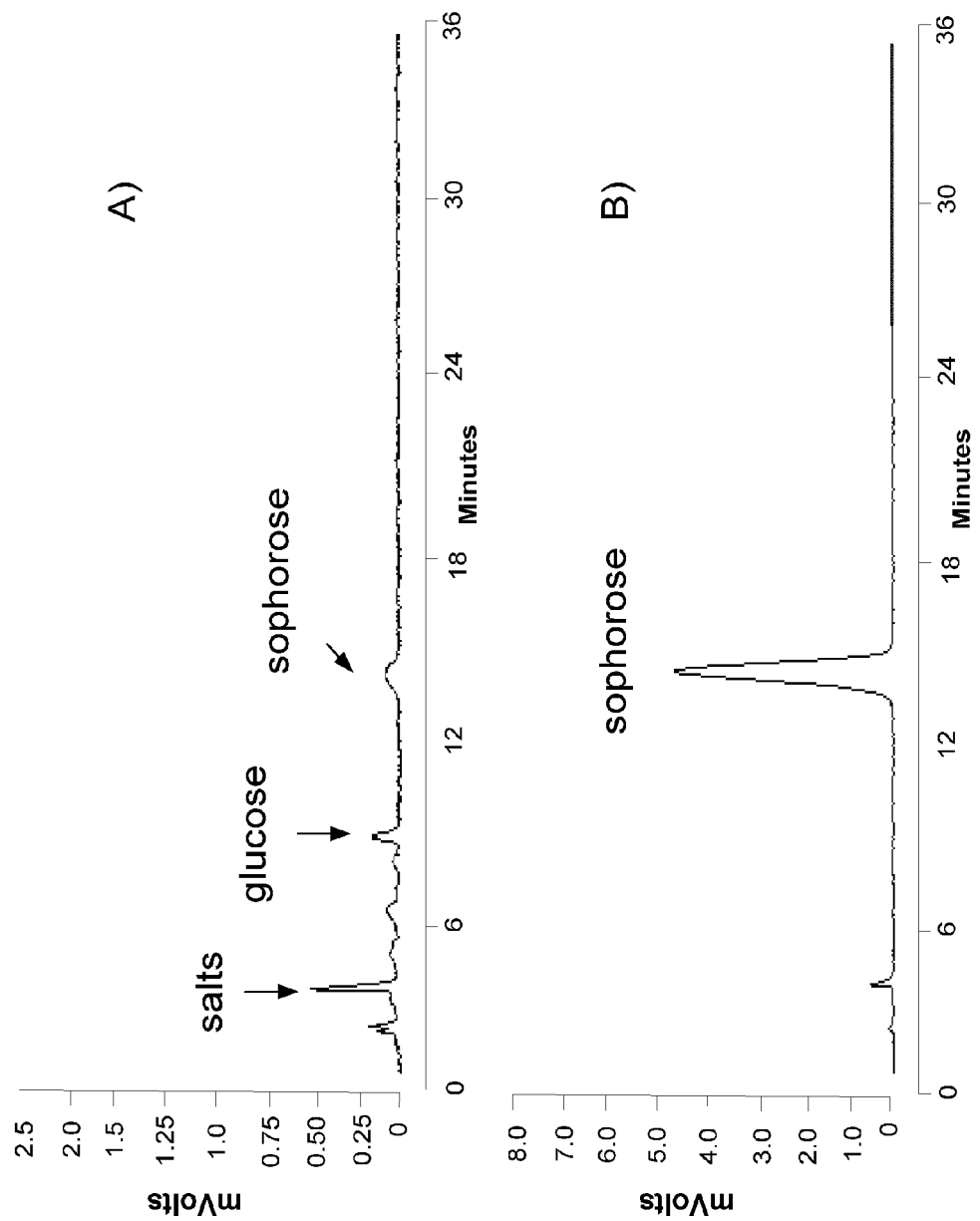
FIG. 14: HPLC-ELSD analysis with a column (X-Bridge Amide (Waters)) with resolution power able to separate hydrophilic compounds (sugars and salts) of the Row A) filtrate after alkaline hydrolysis and filtration Row B) standard of sophorose (sigma).

Alkaline Hydrolysis of Bolaform Sophorolipids for the Production of Sophorose and Acidic Sophorolipids A method was developed by solubilizing 0.5 grams of purified bolaform sophorolipids as described in Example 8 in 30 ml deionized water, bringing the pH of the solution to 9, and incubating this watery solution on a rotating wheel at room temperature for 3 hours, 24 hours and 96 hours. Samples were taken and analyzed on HPLC-ELSD as described under Example 1 and are shown in FIG. 12. As can be clearly seen in the figure, the alkaline pH results in the hydrolysis of the ester bond, giving rise to acidic sophorolipids (peaks at 18-20 minutes) and sophorose (eluting in the dead time with this method (peak at 1-2 minutes)). To separate the acidic sophorolipids from the sophorose, ultrafiltration as described in Example 8 is used. When using a 1-kDa membrane, all the acidic sophorolipids (and remaining bolaform sophorolipids) remained in the retentate, while part of the sophorose was washed away with the washing water and was detected in the filtrate. The latter was confirmed by running a sample of the filtrate on an X-Bridge Amide column (Waters) and analyzed using the Shimadzu ELSD-LT system under the following conditions: mobile phase: 75% acetonitrile+0.15% TEA, 35° C., 1 ml/minute. The injection volume was 10 microliters. A sophorose standard was purchased from Sigma. Both standard and the filtrate (FIG. 13, Row B) were analyzed and the results are shown in FIG. 14. This reaction is further optimized to get optimal conversion of all the bolaform sophorolipids to acidic sophorolipids, without breaking the glycosidic bond connecting the two glucose molecules (detection of glucose). In addition, the ultrafiltration is further optimized, as not all sophorose could be washed away from the retentate by using a 1-kDa cut off membrane (see FIG. 13, Row C).

Example 10

Production of Symmetric Bolaform Sophorolipids Using Fatty Alcohols and/or Diols The strain knocked out in both the acetyltransferase and lactonase gene was used. General culture conditions, sampling and analysis are identical as described for Example 1. Yet, instead of rapeseed oil, either 18 g/L 1-hexadecanol, 1-octadecanol, 1-octadecenol or 1-16 hexadecanediol was added two days after inoculation. If required, an additional amount of 18 g/L hydrophobic substrate was added during the fermentation period. This resulted in the production of symmetric bolaform sophorolipids. The length of the hydrophobic spacer of these new molecules depends on the chain length of the hydrophobic substrate.

If one wants to increase the relative amount of these symmetric bolaform sophorolipids, a strain knocked out in the acetyltransferase and lactonase genes with an additional knock out in the cytochrome P450 monooxygenase gene CYP52M1 (GenBank Accession number ACD75398.1) can also be applied, this combined with the use of 1-16 hexadecanediol or another type of diol. Experimental set-up is identical as described above and the majority of the obtained glycolipids are symmetric bolaform sophorolipids with a spacer of 16 carbon atoms.

REFERENCES

Asmer H. J., S. Lang, F. Wagner, and V. Wray (1988). Microbial production, structure elucidation and bioconversion of sophorose lipids. *J. Am. Oil Chem. Soc.* 65:1460-1466.

Baccile N., F. Babonneau, J. Jestin, G. Pehau-Arnaudet, and I. Van Bogaert (2012). Unusual, pH-Induced, Self-Assembly Of Sophorolipid Biosurfactants. *Acs. Nano* 6:4763-4776.

Banat I. M., A. Franzetti, I. Gandolfi, G. Bestetti, M. G. Martinotti, L. Fracchia, T. J. Smyth, and R. Marchant (2010). Microbial biosurfactants production, applications and future potential. *Appl. Microbiol. Biotechnol.* 87:427-444.

Brakemeier A., S. Lang, D. Wullbrandt, L. Merschel, A. Benninghoven, N. Buschmann, and F. Wagner (1995). Novel sophorose lipids from microbial conversion of 2-alkanols. *Biotechnol. Lett.* 17:1183-1188.

Brakemeier A., D. Wullbrandt, and S. Lang (1998). *Candida bombicola*: production of novel alkyl glycosides based on glucose/2-dodecanol. *Appl. Microbiol. Biotechnol.* 50:161-166.

Chen J., X. Song, H. Zhang, Y. B. Qu, and J. Y. Miao (2006). Production, structure elucidation and anticancer properties of sophorolipid from *Wickerhamiella domercqiae*. *Enzyme Microb. Technol.* 39:501-506.

Franzetti A., E. Tamburini, and I. M. Banat (2010). Applications of biological surface active compounds in remediation technologies. In *Advances in Experimental medicine and biology* Volume 672, S. Ramkrishna (ed)., Springer-Verlag Berlin: Germany; 121-134.

Gheysen K., and K. Conrath (2008). Rapid identification of common hexapyranose monosaccharide units by a simple TOCSY matching approach. *Chem.* 14:8869-8878.

Gorin P. A. J., J. F. T. Spencer, and A. P. Tulloch (1961). Hydroxy fatty acid glycosides of sophorose from *Torulopsis magnoliae*. *Can. J. Chem.* 39:846-855.

Imura T., Y. Masuda, H. Minamikawa, T. Fukuoka, M. Konishi, T. Morita, H. Sakai, M. Abe and D. Kitamoto (2010). Enzymatic conversion of unacetylated sophorose lipid into acetylated glucose lipid: surface-active properties of novel bolaform biosurfactants. *J. Oleo. Sci.* 59:495-501.

Konishi M., T. Fukuoka, T. Morita, T. Imura, and D. Kitamoto (2008). Production of new types of sophorolipids by *Candida batistae*. *J. Oleo. Sci.* 57:359-369.

Kralova I., and J. Sjoblom (2009). Surfactants used in food industry: a review. *J. Disper. Sci. Technol.* 30:1363-1383.

Kurtzman C. P., N. P. J. Price, K. J. Ray, and T. M. Kuo (2010). Production of sophorolipid biosurfactants by multiple species of the *Starmerella* (*Candida*) *bombicola* yeast clade. *FEMS Microbiol. Lett.* 311:140-146.

Kurtzman C. P. (2012). *Candida kuoi* sp nov., an anomorphic species of the *Starmerella* yeast clade that synthesizes sophorolipids. *Int. J. Syst. Evol. Microbiol.* 62:2307-2311.

Mulligan C. N. (2009). Recent advances in the environmental applications of biosurfactants. *Curr. Opin. Colloid. In.* 14:372-378.

Price N. P., K. J. Ray, K. Vermillion, C. A. Dunlap, and C. P. Kurtzman (2011). Structural characterization of novel sophorolipid biosurfactants from a newly identified species of *Candida* yeast. *Carbohydr. Res.* 348:33-41.

Rau U., R. Heckmann, V. Wray, and S. Lang (1999). Enzymatic conversion of a sophorolipid into a glucose lipid. *Biotechnol. Lett.* 21:973-977.

Saerens K., I. Van Bogaert, W. Soetaert, and E. J. Vandamme (2009). Production of glucolipids and specialty fatty acids from sophorolipids by *Penicillium decumbens* naringinase: Optimization and kinetics. *Biotechnol. J.* 4:517-524.

Saerens K. M. J., S. Roelants, I. N. A. Van Bogaert, and W. Soetaert (2011a).

Identification of the UDP-glucosyltransferase gene UGTA1, responsible for the first glucosylation step in the sophorolipid biosynthetic pathway of *Candida bombicola* ATCC22214. *FEMS Yeast Res.* 11:123-132.

Saerens K., S. Saey, and W. Soetaert (2011b). One-step production of unacetylated sophorolipids by an acetyltransferase negative *Candida bombicola*. *Biotechnol. Bioengin.* 108:2923-2931.

Saerens K., J. Zhang, L. Saey, I. N. Van Bogaert, and W. Soetaert (2011c). Cloning and functional characterization of the UDP-glucosyltransferase UgtB1 involved in sophorolipid production by *Candida bombicola* and creation of a glucolipid-producing yeast strain. *Yeast* 28:279-292.

Spencer J. F. T., P. A. J. Gorin, and A. P. Tulloch (1970). *Torulopsis bombicola* sp. n. *A. Van Leeuw. J. Microb. Ser.* 36:129-133.

Tulloch A. P., J. F. T. Spencer, and M. H. Deinema (1968a). A new hydroxy fatty acid sophoroside from *Candida bogoriensis*. *Can. J. Chem.* 46:345-348.

Van Bogaert I. N. A., S. L. De Maeseneire, D. Develter, W. Soetaert, and E. J. Vandamme (2008a). Development of a transformation and selection system for the glycolipid producing yeast *Candida bombicola*. *Yeast* 25:272-278.

Van Bogaert I. NA., S. Fleurackers, S. Van Kerrebroeck, D. Develter, and W. Soetaert (2011). Production of new-to-nature sophorolipids by cultivating the yeast *Candida bombicola* on unconventional hydrophobic substrates. *Biotechnology and Bioengineering* 108:734-741.

The invention claimed is:

1. A method of producing bolaamphiphilic glycolipids having a hydrophobic spacer with hydrophilic glucose molecules at both ends of the spacer, the method comprising:
   growing a yeast strain that comprises a dysfunctional acetyltransferase and a dysfunctional lactonase in a fermentation broth, and
   recovering bolaamphiphilic glycolipids produced by the yeast strain from the fermentation broth,
   wherein the yeast strain is *Starmerella bombicola* ATCC 22214, and
   wherein the dysfunctional acetyltransferase is produced by:
      mutating a gene in the yeast strain encoding the acetyltransferase and the lactonase,
      silencing transcription or translation of a gene in the yeast strain encoding the acetyltransferase and the lactonase, and/or
      disrupting the function of the acetyltransferase and the lactonase in the yeast strain, and
   wherein the total amount of the bolaamphiphilic glycolipids produced is at least 10% of the total amount of several types of glycolipids produced.

2. The method according to claim 1, wherein the yeast strain further comprises a dysfunctional glucosyltransferase, which is responsible for the second glucosylation step in the sophorolipid biosynthetic pathway.

3. A method of producing bolaamphiphilic glycolipids having a hydrophobic spacer with hydrophilic glucose molecules at both ends of the spacer, the method comprising:
   culturing a yeast strain comprising a dysfunctional acetyltransferase and a dysfunctional lactonase in a broth, wherein the yeast strain is *Starmerella bombicola* ATCC 22214, in order to obtain a fermentation broth comprising a mixture of several types of glycolipids; and
   recovering the bolaamphiphilic glycolipids from the fermentation broth,
   wherein the total amount of the bolaamphiphilic glycolipids produced is at least 10% of the total amount of several types of glycolipids produced.

4. The method according to claim 3, wherein the yeast strain further comprises:
   a dysfunctional glucosyltransferase that is responsible for the second glucosylation step in the sophorolipid biosynthetic pathway.

5. The method according to claim 3, wherein the bolaamphiphilic glycolipids are recovered from the fermentation broth with an organic solvent.

6. The method according to claim 5, wherein the organic solvent comprises methanol and/or ethanol.

7. The method according to claim 3, wherein the bolaamphiphilic glycolipids are recovered from the fermentation broth using a membrane filtration technique.

8. The method according to claim 7, wherein the membrane filtration technique is ultrafiltration or diafiltration.

9. The method according to claim 4, wherein any dysfunctional acetyltransferase, lactonase, and/or glucosyltransferase responsible for the second glucosylation step in the sophorolipid biosynthetic pathway is produced by:
   mutating gene(s) encoding the acetyltransferase, lactonase and/or glucosyltransferase, or
   silencing transcription or translation of gene(s) encoding the acetyltransferase, lactonase, and/or glucosyltransferase, and/or
   disrupting the function of the acetyltransferase, lactonase, and/or glucosyltransferase.

10. The method according to claim 4, wherein the yeast strain comprises:
    a dysfunctional acetyltransferase and a dysfunctional lactonase, and
    wherein the bolaamphiphilic glycolipids are non-acetylated, bolaamphiphilic glycolipids consisting of four (4) glucose molecules.

11. The method according to claim 4,
    wherein the bolaamphiphilic glycolipids are non-acetylated bolaamphiphilic glycolipids consisting of two (2) glucose molecules, and
    wherein the yeast strain comprises:
       a dysfunctional acetyltransferase, a dysfunctional glucosyltransferase responsible for the second glucosylation step in the sophorolipid biosynthetic pathway, and a dysfunctional lactonase.

12. The method according to claim 3, further comprising: performing an alkaline hydrolysis of the bolaamphiphilic glycolipids produced thereby so as to produce sophorose and acidic sophorolipids.

13. A method of producing symmetric bolaamphiphilic glycolipids having a hydrophobic spacer with hydrophilic glucose molecules at both ends of the spacer, wherein the hydrophilic glucose molecules are linked to both sides of the spacer by a glycosidic bond, the method comprising:
    culturing yeast strain *Starmerella bombicola* ATCC 22214, in a fermentation broth wherein the yeast strain comprises:
        a dysfunctional acetyltransferase and a dysfunctional lactonase, or
        a dysfunctional acetyltransferase, a dysfunctional lactonase, and a dysfunctional cytochrome P450 monooxygenase,
    adding fatty alcohols and/or diols as a substrate in the fermentation broth in order to obtain a fermentation broth comprising a mixture of several types of glycolipids, and
    recovering the symmetric bolaamphiphilic glycolipids from the fermentation broth.

14. The method according to claim 4, wherein the glucosyltransferase is encoded by gene GenBank Accession Number HM440974.

* * * * *

SEQUENCE LISTING

<160> NUMBER OF SEQ ID NOS: 4

<210> SEQ ID NO 1
<211> LENGTH: 28
<212> TYPE: DNA
<213> ORGANISM: Artificial sequence
<220> FEATURE:
<223> OTHER INFORMATION: primer

<400> SEQUENCE: 1
cagcagagac catctgccta gcaacttc                                28

<210> SEQ ID NO 2
<211> LENGTH: 20
<212> TYPE: DNA
<213> ORGANISM: Artificial sequence
<220> FEATURE:
<223> OTHER INFORMATION: primer

```
-continued

<400> SEQUENCE: 2
gccactgcca ttggagattg                                                       20

<210> SEQ ID NO 3
<211> LENGTH: 23
<212> TYPE: DNA
<213> ORGANISM: Artificial sequence
<220> FEATURE:
<223> OTHER INFORMATION: primer

<400> SEQUENCE: 3
ttcgacagcg tctccgacct gat                                                   23

<210> SEQ ID NO 4
<211> LENGTH: 22
<212> TYPE: DNA
<213> ORGANISM: Artificial sequence
<220> FEATURE:
<223> OTHER INFORMATION: primer

<400> SEQUENCE: 4
tggtctggcc ctgagtctga ag                                                    22
```